US007304205B2

(12) United States Patent
Choe et al.

(10) Patent No.: US 7,304,205 B2
(45) Date of Patent: Dec. 4, 2007

(54) DWF12 AND MUTANTS THEREOF

(75) Inventors: Sunghwa Choe, Seoul (KR); Kenneth A. Feldmann, Newbury Park, CA (US); Frans Tax, Tucson, AZ (US)

(73) Assignee: The Arizona Board of Regents on Behalf of the University of Arizona, Tucson, AZ (US)

( * ) Notice: Subject to any disclaimer, the term of this patent is extended or adjusted under 35 U.S.C. 154(b) by 348 days.

(21) Appl. No.: 10/477,687

(22) PCT Filed: May 15, 2002

(86) PCT No.: PCT/US02/15563

§ 371 (c)(1),
(2), (4) Date: Oct. 15, 2004

(87) PCT Pub. No.: WO02/092777

PCT Pub. Date: Nov. 21, 2002

(65) Prior Publication Data

US 2005/0049397 A1 Mar. 3, 2005

Related U.S. Application Data

(60) Provisional application No. 60/291,342, filed on May 16, 2001.

(51) Int. Cl.
 C12N 15/82 (2006.01)
 A01H 5/00 (2006.01)
(52) U.S. Cl. ................. 800/278; 800/298; 800/287; 800/290
(58) Field of Classification Search ............ 526/23.1, 526/23.6; 435/320.1; 800/278, 290, 287, 800/298
See application file for complete search history.

(56) References Cited

U.S. PATENT DOCUMENTS

| 4,801,340 | A | 1/1989 | Inoue et al. |
| 5,034,323 | A | 7/1991 | Jorgensen et al. |
| 5,231,020 | A | 7/1993 | Jorgensen et al. |
| 5,283,184 | A | 2/1994 | Jorgensen et al. |
| 5,759,829 | A | 6/1998 | Shewmaker et al. |
| 6,787,687 | B1* | 9/2004 | Giovannoni et al. ..... 800/317.4 |
| 2004/0009476 | A9* | 1/2004 | Harper et al. ................. 435/6 |

FOREIGN PATENT DOCUMENTS

| EP | 1 033 405 | 9/2000 |
| WO | WO 00/47715 | 8/2000 |

OTHER PUBLICATIONS

Zhou et al (2004, The Plant Journal 40:399-409).*
Bowie et al, Science 247:1306-1310, 1990.*
McConnell et al, Nature 411 (6838):709-713, 2001.*

Dornelas et al., "*Arabidopsis thaliana* SHAGGY-related protein kinases (AtSK11 and 12) function in perianth and gynoecium development," *Plant J.*, 2000, 21(5):419-429.
Dornelas et al., "Characterization of three novel members of the *Arabidopsis* SHAGGY-related protein kinase (ASK) multigene family," *Plant Mol. Biol.*, 1999, 39(1):137-147.
Piao et al., "Constitutive over-expression of AtGSK1 induces NaCl stress responses in the absence of NaCl stress and results in enhanced NaCl tolerance in *Arabidopsis*," *Plant J.*, 2001, 27(4):305-314.
GenBank Accession No. X94939 dated Jan. 18, 1996 (updated Feb. 13, 1998).
GenBank Accession No. AAG44601 dated Oct. 18, 2000.
Adams et al., "Hindered Dialkylamino Nucleoside Phosphite Reagents in the Synthesis of Two DNA 51-Mers," *J. Am. Chem. Soc.*, 1983, 105:661-663.
Altmann, "A Tale of Dwarfs and Drugs: Brassinosteroids to the Rescue," Trends Genet., 1998, 14:490-495.
Azpiroz et al., "An *Arabidopsis* Brassinosteroid-Dependent Mutant is Blocked in Cell Elongation," *Plant Cell*, 1998, 10:219-230.
Bakkeren et al., "Recovery of *Agrobacterium tumefaciens* T-DNA molecules from whole plants early after transfer," *Cell*, 1989, 57(5):847-857.
Bevan, "Binary *Agrobacterium* vectors for plant transformation," *Nucl. Acids. Res.*, 1984, 12(22):8711-8721.
Bevan and Chilton, "T-DNA of the Agrobacterium TI and RI Plasmids," *Ann. Rev. Genet.*, 1982, 16:357-384.
Bianchi et al., "*Arabidopsis* homologs of the *shaggy* and and GSK-3 protein kinases: molecular cloning and functional expression in *Escherichia coli*," *Mol. Gen. Genet.*, 1994, 242:337-345.
Binding, "Regeneration of Plants", *Plant Protoplasts*, 1985, CRC Press, Boca Raton, pp. 21-73.
Boulton et al., "Specificity of *Agrobacterium*-mediated delivery of maize streak virus DNA to members of the Gramineae," *Plant Mol. Biol.*, 1989, 12:31-40.
Brisson et al., "Expression of a bacterial gene in plants by using a viral vector," *Nature*, 1984, 310:511-514.
Broglie et al., "Light-Regulated Expression of a Pea Ribulose-1,5-Bisphosphate Carboxylase Small Subunit Gene in Transformed Plant Cells," *Science*, 1984, 224:838-843.
Bustos et al., "Regulation of β-Glucuronidase Expression in Transgenic Tobacco Plants by an A/T-Rich, *cis*-Acting Sequence Found Upstream of a French Bean β-Phaseolin Gene," *Plant Cell*, 1989, 1:839-853.
Carruthers et al., "Chemical Synthesis and Biological Studies on Mutated Gene-control Regions," *Cold Spring Harbor Symp. Quant. Biol.*, 1983, 47:411-418.
Choe et al., "The *Arabidopsis* Dwarf1 Mutant is Defective in the Conversion of 24-methylenecholesterol to Campesterol in Brassinosteroid Biosynthesis," *Plant Physiol.*, 1999, 119:897-907.
Choe et al., "The *Arabidopsis* Dwf7/ste1 Mutant is Defective in the $\Delta^7$ Sterol C-5 Desaturation Step Leading to Brassinosteroid Biosynthesis," *Plant Cell*, 1999, 11:207-221.

(Continued)

*Primary Examiner*—Stuart F. Baum
(74) *Attorney, Agent, or Firm*—Fish & Richardson P.C.

(57) ABSTRACT

DWARF12(DWF12) sequences, mutants and methods of using the same are disclosed. The dwf12 polynucleotides can be used in the production of transgenic plants which display at least one dwf12 mutant phenotype, so that the resulting plants have altered biochemistry, structure or morphology.

12 Claims, 8 Drawing Sheets

OTHER PUBLICATIONS

Choe et al., "*Arabidopsis* Brassinosteroid-Insensitive *dwarf12* Mutants Are Semidominant and Defective in a Glycogen Synthase Kinase 3β-Like Kinase," *Plant Physiol.*, 2002, 130:1506-1515.

Clark-Lewis et al., "Chemical Synthesis, Purification, and Characterization of Two Inflammatory Proteins, Neutrophil Activating Peptide 1 (Interleukin-8) and Neutrophil Activating Peptide 2," *Biochem.*, 1991, 31:3128-3135.

Clouse et al., "Brassinosteroids: Essential Regulators of Plant Growth and Development," *Annu. Rev. Plant Physiol. Plant Mol. Biol.*, 1998, 49:427-451.

Clouse et al., "A Brassinosteroid-insensitive Mutant in *Arabidopsis thaliana* Exhibit Multiple Defects in Growth and Developments," *Plant Physiol.*, 1996, 111:671-678.

Clouse et al., "Molecular Genetics of Brassinosteroid Action. In Brassinosteroids: Steroidal Plant Hormones," 1999, Springer, Tokyo, Japan, pp. 163-190.

Coruzzi et al., "Tissue-specific and light-regulated expression of a pea nuclear gene encoding the small subunit of ribulose-1,5-bisphosphate carboxylase," *EMBO J.*, 1984, 3(8):1671-1679.

Creighton, "Amino Acid Composition," *Proteins, Structures and Molecular Principles*, 1983, W.H. Freeman and Co., NY, pp. 34-60.

Decroocq-Ferrant et al., "*Petunia hybrida* homologues of shaggy/zeste-white 3 expressed in female and male reproductive organs," *Plant J.*, 7(6):897-911.

D'Halluin et al., "Transgenic Maize Plants by Tissue Electroporation," *Plant Cell*, 1992, 4:1495-1505.

Dornelas et al., "Three New cDNAs Related to SGG/GSK-3 (SHAGGY/Glycogen Synthase Kinase-3) from *Arabidopsis thaliana* (Accession Nos. X94938, X94939, and X99696)," *Plant Physiol.*, 1997, 113:306.

Dornelas et al., "The *Arabidopsis* SHAGGY-related protein kinase (ASK) gene family: structure, organization and evolution," *Gene*, 1998, 212:249-257.

Elinzenberger et al., "Isolation and expression during pollen development of a tobacco cDNA clone encoding a protein kinase homologous to shaggy/glycogen synthase kinase-3," *Biochim. Biophys. Acta*, 1995, 1260:315-319.

Evans and Bravo, "Protoplast Isolation and Culture," *Handbook of Plant Cell Culture*, 1983, Macmillan Publishing Co., New York, pp. 124-176.

Feldmann et al., "A dwarf Mutant of *Arabidopsis* Generated by T-DNA Insertion Mutagenesis," *Science*, 1989, 243:1351-1354.

Fraley et al., "Expression of Bacterial Genes in Plant Cells," *Proc. Natl. Acad. Sci. USA*, 1983, 80:4803-4807.

Fromm et al., "Expression of Genes Transferred into Monocot and Dicot Plant Cells by Electroporation," *Proc. Natl. Acad. Sci. USA*, 1985, 82:5824-5828.

Gachotte et al., "An *Arabidopsis* Mutant Deficient in Sterol Biosynthesis: Heterologous Complementation by ERG3 Encoding a $\Delta^7$-sterol-C-5-Desaturase From Yeast," *Plant J.*, 1995, 8:407-416.

Gachotte et al., "Isolation and Characterization of an *Arabidopsis thaliana* cDNA Encoding a $\Delta^7$-sterol-C-5-Desaturase by Functional Complementation of a Defective Yeast Mutant," *Plant J.*, 1996, 9:391-398.

Gordon-Kamm et al., "Transformation of Maize Cells and Recognition and Regeneration of Fertile Transgenic Plants," *Plant Cell*, 1990, 2:603-618.

Gould et al., "Transformation of *Zea mays* L. Using *Agrobacterium tumefaciens* and the Shoot Apex," *Plant Physiol.*, 1991, 95:426-434.

Green et al., "Binding site requirements for pea nuclear protein factor GT-1 correlate with sequences required for light-dependent transcriptional activation of the *rbcS-3A* gene," *EMBO J.*, 1988, 7:4035-4044.

Grierson & Covey, "Genetic Transformation of Plants by *Agrobacterium*," "Plant Viruses," and "Genetic Engineering of Plants," *Plant Mol. Biol.*, 1988, 2nd edition, Blackie and Son Ltd., London, Chapters 7-9.

Grimsley et al., "DNA transfer from Agrobacterium to *Zea mays* or Brassica by agroinfection is dependent on bacterial virulence functions," *Mol. Gen. Genet.*, 1989, 217:309-316.

Gurley et al., *Mol. Cell Biol.*, "Upstream Sequences Required for Efficient Expression of a Soybean Heat Shock Gene," 1986, 6(2):559-565.

Haseloff and Gerlach, "Simple RNA enzymes with new and highly specific endoribonuclease activities," *Nature*, 1988, 334:585-591.

Hernalsteens et al., "An *Agrobacterium*-transformed cell culture from the monocot *Asparagus officinalis*," *EMBO J.*, 1984, 3(13):3039-3041.

Hooykaas-Van Slogteren et al., "Expression of Ti plasmid genes in monocotyledonous plants infected with *Agrobacterium tumefaciens*," *Nature*, 1984, 311:763-764.

Horsch et al., *Science*, "A Simple and General Method for Transferring Genes into Plants," 1985, 227:1229-1231.

Husselstein et al., "$\Delta^7$-sterol-C5-Desaturase: Molecular Characterization and Functional Expression of Wild-type and Mutant Allelles," *Plant Mol. Biol.*, 1999, 39:891-906.

Jonak et al., "Inflorescence-specific expression of AtK-1, a novel *Arabidopsis thaliana* homologue of shaggy/glycogen synthase kinase-3," *Plant Mol. Biol.*, 1995, 27:217-221.

Jordano et al., "A Sunflower Helianthinin Gene Upstream Sequence Ensemble Contains an Enhancer and Sites of Nuclear Protein Interaction," *Plant Cell*, 1989, 1:855-866.

Kaeppler et al., "Silicon carbide fiber-mediated DNA delivery into plants cells," *Plant Cell Reports*, 1990, 9:415-418.

Klahre et al., "The Arabidopsis DIMINUTO/DWARF1 Gene Encodes a Protein Involved in Steroid Synthesis," *Plant Cell*, 1998, 10:1677-1690.

Klee et al., "*Agrobacterium*-Mediated Plant Transformation and Its Further Applications to Plant Biology," *Ann. Rev. of Plant Physiol.*, 1987, 38:467-486.

Klein et al., "High-velocity microprojectiles for delivering nucleic acids into living cells," *Nature*, 1987, 327:70-73.

Klein et al., "Transfer of foreign genes into intact maize cells with high-velocity microprojectiles," *Proc. Natl. Acad. Sci. USA*, 1988, 85:4305-4309.

Li et al., "Conservation of Function Between Mammalian and Plant Steroid 5-Reductases," *Proc. Natl. Acad. Sci. USA*, 1997, 94:3554-3559.

Li and Nam, "Regulation of Brassinosteroid Signaling by a GSK3/SHAGGY-Like Kinase," *Science*, 2002, 295:1299-1301.

Meier et al., "Elicitor-Inducible and Constitutive in Vivo DNA Footprints Indicate Novel *cis*-Acting Elements in the Promoter of a Parsley Gene Encoding Pathogenesis-Related Protein 1," *Plant Cell*, 1991, 3:309-315.

Merrifield, "Sold Phase Peptide Synthesis. I. The Synthesis of a Tetrapeptide," *J. Am. Chem. Soc.*, 1963, 85:2149-2156.

Messing et al., "Plant Gene Structure," *Genetic Engineering of Plants*, 1983, Plenum Press, New York, NY pp. 211-227.

Napoli et al., "Introduction of a Chimeric Chalcone Synthase Gene into Petunia Results in Reversible Co-Suppression of Homologous Genes *in trans*," *The Plant Cell*, 1990, 2:279-289.

Noguchi et al., "Brassinosteroid-Insensitive (bri1) Dwarf Mutants of *Arabidopsis* Accumulate Brassinosteroids," *Plant Physiol.*, 1999, 121:743-752.

Nomura et al., "Brassinosteroid/Sterol Synthesis and Plant Growth as Affected by lka and lkb Mutations of Pea," *Plant Physiol.*, 1999, 119:1517-1526.

Paszkowski et al., "Direct gene transfer to plants," *EMBO J.*, 1984, 3(12):2717-2722.

Pay et al., *Plant J.*, "The *MsK* family of alfalfa protein kinase genes encodes homologues of *shaggy/glycogen synthase kinase-3* and shows differential expression patterns in plant organs and development," 1993, 3(6):847-856.

Pérez-Pérez et al., "The UCU1 *Arabidopsis* Gene Encodes a SHAGGY/GSK3-like Kinase Required for Cell Expansion along the Proximodistal Axis," *Dev. Biol.*, 2002, 242:161-173.

Potrykus et al., "Molecular and general genetics of a hybrid foreign gene introduced into tobacco by direct gene transfer," *Mol. Gen. Genet.*, 1985, 199:169-177.

Rogers et al., "Gene Transfer in Plants" Production of Transformed Plants Using Ti Plasmid Vectors, *Methods Enzymol.*, 1986, 118:627-641.

Rogers et al., "Gene Transfer in Plants: Production of Transformed Plants Using Ti Plasmid Vectors," *Methods for Plant Molecular Biology*, 1988, Academic Press, San Diego, CA, pp. 423-463.

Schwartz and Dayhoff, "Matrices for Detecting Distant Relationships," *Atlas of Protein Sequence and Structure*, 1978, 3 suppl., 5:353-358, National Biomedical Research Foundation, Washington, DC.

Shah et al., "Engineering Herbicide Tolerance in Transgenic Plants," Science, 1986, 233:478-481.

Sheehy et al., "Reduction of polygalacturonase activity in tomato fruit by antiense RNA," *Proc. Natl. Acad. Sci. USA*, 1988, 85:8805-8809.

Shimamoto et al., "Fertile transgenic rice plants regenerated from transformed protoplasts," *Nature*, 1989, 338:274-276.

Sikorski and Boeke, "In Vitro Mutagenesis and Plasmid Shuffling: From Cloned Gene to Mutant Yeast," *Meth. Enzymol.*, 1991, 194:302-318.

Smith and Waterman, "Comparison of Biosequences," *Adv. Appl. Math.*, 1981, 2:482-489.

Takahashi et al., "The DIMINUTO Gene of *Arabidopsis* is Involved in Regulating Cell Elongation," *Genes Dev.*, 1995, 9:97-107.

Takamatsu et al., "Expression of bacterial chloramphenicol acetyltransferase gene in tobacco plants mediated by TMV-RNA," *EMBO J.*, 1987, 6(2):307-311.

Weising et al., "Foreign Genes in Plants: Transfer, Structure, Expression, and Applications," *Annu. Rev. Genet.*, 1988, 22:421-477.

Zhang et al., "DNA Sequences That Activate Isocitrate Lyase Gene Expression during Late Embryogenesis and during Postgerminative Growth," *Plant Physiol.*, 1996, 110:1069-1079.

GenBank Accession No. X94939, Feb. 13, 1998.
GenBank Accession No. X94938, Feb. 13, 1998.
GenBank Accession No. X99696, Feb. 13, 1998.
GenBank Accession No. AF019927, May 14, 1999.
GenBank Accession No. Y13437, Feb. 16, 1998.
GenBank Accession No. X75431, Feb. 10, 1999.
GenBank Accession No. X83619, Sep. 18, 1995.
GenBank Accession No. AB059621, Apr. 14, 2001.
GenBank Accession No. X77763, Jul. 6, 1995.
GenBank Accession No. X75432, Mar. 15, 1994.
GenBank Accession No. X68525, Jan. 8, 1997.
GenBank Accession No. X68411, Sep. 9, 2004.
GenBank Accession No. X68409, Sep. 9, 2004.
GenBank Accession No. X68410, Sep. 9, 2004.
GenBank Accession No. Y07822, Nov. 24, 1998.
GenBank Accession No. Y08607, Oct. 8, 1996.
GenBank Accession No. AJ224163, Nov. 24, 1998.
GenBank Accession No. Y12674, Nov. 24, 1998.
GenBank Accession No. AJ002315, Nov. 24, 1998.
GenBank Accession No. X83620, Feb. 24, 1998.
GenBank Accession No. AJ002314, Nov. 24, 1998.
GenBank Accession No. X99100, Jul. 11, 1996.
GenBank Accession No. AJ295939, Sep. 26, 2000.
GenBank Accession No. Y07597, Aug. 22, 1996.
GenBank Accession No. Y08947, Oct. 22, 1996.
GenBank Accession No. AJ002280, Nov. 24, 1998.
GenBank Accession No. BM543509, Feb. 19, 2002.
GenBank Accession No. AJ131048, Nov. 25, 1998.
GenBank Accession No. CAB37456, dated Mar. 25, 1999.

* cited by examiner

Translation of the DWF12 genomic DNA

```
                10                    30                    50
                 .                     .                     .
      AGAAAGAGAAAGAGAAGAGCTGGATTCACATGGTCTTGTTCTTTCTCTCTCCTTCTTTTC
      TCTTTCTCTTTCTCTTCTCGACCTAAGTGTACCAGAACAAGAAAGAGAGAGGAAGAAAAG 70                    90                   110
                 .                     .                     .
      TCATCTTGCGGCTTCCCTTTCTCTCTCTATCGCCACAATGATCATTACCAACCAAACTGA
      AGTAGAACGCCGAAGGGAAAGAGAGAGATAGCGGTGTTACTAGTAATGGTTGGTTTGACT 130                  150                   170
                 .                     .                     .
      TTGAAACTCATTTGTTCTCTCTCTCTCAAATCCACTCTCTCTCTTTCTTTTCTCTTCTCC
      AACTTTGAGTAAACAAGAGAGAGAGAGTTTAGGTGAGAGAGAGAAAGAAAAGAGAAGAGG

D12-OVF1
                190                   210                  230
                 .  GAAT               .                    .
      TCTCTGTGTCTCTATCGCCATGGCTGATGATAAGGTAAAGCTGCTTGTGTTCCTTTTGCT

TCTCTGTGTCTCTATCGCCATGGCTGATGATAAGGTAAAGCTGCTTGTGTTCCTTTTGCT    E1
      AGAGACACAGAGATAGCGGTACCGACTACTATTCCATTTCGACGAACACAAGGAAAACGA
                           M  A  D  D  K 250                  270                   290
                 .                    .                     .
      GTCTTTTGAAGAAGAAGATCCTGTTTTTTGGTTTTTCCACATTTGACCCTTCAATTAGTT
      CAGAAAACTTCTTCTTCTAGGACAAAAAACCAAAAAGGTGTAAACTGGGAAGTTAATCAA 310                  330                   350
                 .                    .                     .
      GTCTTGAGATTCCTGTTCTTACAGATGTTTTGTGATAATAAATCTAGTTTAGTTAGTACT
      CAGAACTCTAAGGACAAGAATGTCTACAAAACACTATTATTTAGATCAAATCAATCATGA 370                  390                   410
                 .                    .                     .
      CTTGAAGTTGAACGGTTTTGAGTTCTGGGTTTGTCCAAAGTTTTGAGCTTTCGTTAACTT
      GAACTTCAACTTGCCAAAACTCAAGACCCAAACAGGTTTCAAAACTCGAAAGCAATTGAA

120F2
                430                   450                   470
                 .                     .                     .
      TTTGACTTACCCTGAGATCTCTGAGGGTTTTGAGTTCTGAGCTTAGAATTTTCTAAGTTA
      AAACTGAATGGGACTCTAGAGACTCCCAAAACTCAAGACTCGAATCTTAAAAGATTCAAT 490                  510                   530
                 .                    .                     .
      GCTCTGTTGGGATGATCCATGTCTATATATCTCGATCTGTGATTAATCCAGAGTTTATAC
      CGAGACAACCCTACTAGGTACAGATATATAGAGCTAGACACTAATTAGGTCTCAAATATG 550                  570                   590
                 .                    .                     .
      AAGCTGCTAGATCCATAATTGAACATAGATTAGTCCTTGTTTGGTTTGTTATATGTATTT
```

FIG. 1A

TTCGACGATCTAGGTATTAACTTGTATCTAATCAGGAACAAACCAAACAATATACATAAA

```
             610                 630                 650
              .                   .                   .
GTTTTGTTTACCATTCTTTTGGCGTGACAAAAGTATATATTTTTAGTTTTAACTAAATCA
CAAAACAAATGGTAAGAAAACCGCACTGTTTTCATATATAAAAATCAAAATTGATTTAGT 670                 690                 710
              .                   .                   .
GATTCACTCTGCGTAACGGTTATTTTGTAACCACTCTTTTAGGATAAAAGTTTCCTTCTT
CTAAGTGAGACGCATTGCCAATAAAACATTGGTGAGAAAATCCTATTTTCAAAGGAAGAA 730                 750                 770
              .                   .                   .
TAGACTTTTGATTCTCAGACAAGCATTATTCTTTTAGCTTTTGATAATGGTTTTGTGCTG
ATCTGAAAACTAAGAGTCTGTTCGTAATAAGAAAATCGAAAACTATTACCAAAACACGAC 790                 810                 830
              .                   .                   .
ATATTAAAGCTTTTCTCTTTCAGGAGATGCCTGCTGCTGTAGTTGATGGACATGATCAAG    E2
TATAATTTCGAAAAGAGAAAGTCCTCTACGGACGACGACATCAACTACCTGTACTAGTTC
                         E  M  P  A  A  V  V  D  G  H  D  Q  V

┌─────────┐
             850                 870     │    2    │  890
              .                   .      │    .    │   .
TCACTGGTCATATTATTTCCACCACAATCGGTGGCAAAAATGGTGAACCAAAACAGGTAT
AGTGACCAGTATAATAAAGGTGGTGTTAGCCACCGTTTTTACCACTTGGTTTTGTCCATA
   T  G  H  I  I  S  T  T  I  G  G  K  N  G  E  P  K  Q 910                 930                 950
              .                   .                   .
TTTTAAGGCTTTTAACCAAATAGACTCACTTTTATGTATATGCAAGATTTTGATGGTTAC
AAAATTCCGAAAATTGGTTTATCTGAGTGAAAATACATATACGTTCTAAAACTACCAATG sggf3
             970                 990                1010
              .                   .                   .
CAATACATTTTTCTATGTTGTTGTTAGACAATTAGTTACATGGCGGAGCGAGTTGTTGGT
GTTATGTAAAAAGATACAACAACAATCTGTTAATCAATGTACCGCCTCGCTCAACAACCA
                                  T  I  S  Y  M  A  E  R  V  V  G ┌─────────┐
             1030                1050    │   3.    │ 1070
              .                   .      │    .    │   .
ACAGGCTCGTTCGGGATCGTTTTCCAAGCAAAATGTTTGGAGACTGGAGAAACCGTGGCG
TGTCCGAGCAAGCCCTAGCAAAAGGTTCGTTTTACAAACCTCTGACCTCTTTGGCACCGC
   T  G  S  F  G  I  V  F  Q  A  K  C  L  E  T  G  E  T  V  A sgyf2
             1090            1110                1130
              .                .                   .
ATAAAGAAGGTTTTGCAAGATAGAAGATACAAGAACCGAGAACTTCAGTTGATGCGTGTG
TATTTCTTCCAAAACGTTCTATCTTCTATGTTCTTGGCTCTTGAAGTCAACTACGCACAC
   I  K  K  V  L  Q  D  R  R  Y  K  N  R  E  L  Q  L  M  R  V
```

FIG. 1B

```
                1150                    1170                    1190
                 .                       .                       .
ATGGATCATCCGAATGTGGTTTGTTTGAAGCATTGCTTCTTTTCGACTACAAGTAAAGAC
TACCTAGTAGGCTTACACCAAACAAACTTCGTAACGAAGAAAAGCTGATGTTCATTTCTG
 M  D  H  P  N  V  V  C  L  K  H  C  F  F  S  T  T  S  K  D 1210                    1230                    1250
                 .                       .                       .
GAGCTTTTCTTGAACTTGGTTATGGAGTATGTCCCTGAGAGCTTGTATCGAGTTCTGAAA
CTCGAAAAGAACTTGAACCAATACCTCATACAGGGACTCTCGAACATAGCTCAAGACTTT
 E  L  F  L  N  L  V  M  E  Y  V  P  E  S  L  Y  R  V  L  K 1270                    1290                    1310
                 .                       .                       .
CATTATAGTAGTGCAAACCAAAGAATGCCTCTTGTCTATGTTAAACTTTACATGTATCAG
GTAATATCATCACGTTTGGTTTCTTACGGAGAACAGATACAATTTGAAATGTACATAGTC
 H  Y  S  S  A  N  Q  R  M  P  L  V  Y  V  K  L  Y  M  Y  Q 1330                    1350                    1370
                 .                       .                       .
GTAATAACAACACACATTCATATCTTCCATTTCCAAAGTTGATGTACATAAGATTGTTCT
CATTATTGTTGTGTGTAAGTATAGAAGGTAAAGGTTTCAACTACATGTATTCTAACAAGA

120r2
                1390                    1410                    1430
                 .                       .                       .
TATGCTGATATTACTTCCTTTTGTTATGTTAGATCTTCCGGGGACTTGCTTACATTCACA
ATACGACTATAATGAAGGAAAACAATACAATCTAGAAGGCCCCTGAACGAATGTAAGTGT
                  I  F  R  G  L  A  Y  I  H  N 1450                    1470                    1490
                 .                       .                       .
ATGTTGCTGGAGTTTGT  CAG AGATCTAAAGCCTCAAAATCTTCTGGTATGTGTAACAT
TACAACGACCTCAA    CAGTGTC TCTAGATTTCGGAGTTTTAGAAGACCATACACATTGTA
 V  A  G  V   H  P  D  L  K  P  Q  N  L  L

120f4
                1510                    1530                    1550
                 .                       .                       .
TTTAAGATTGAACTCTTTGTTTTTTTTCTTGCCTTTGTTTCTTTCGTTCTTAATGTATCT
AAATTCTAACTTGAGAAACAAAAAAAAGAACGGAAACAAAGAAAGCAAGAATTACATAGA 1570                    1590                    1610
                 .                       .                       .
CTTCTGGTCTCTTTCTATAGGTTGATCCTCTTA CTCA CAA GTCAAAATCTGTGACTTTG
GAAGACCAGAGAAAGATATCCAACTAGGAGAAT GAGTAGTT CAGTTTTAGACACTGAAAC
                    V  D  P  L  T   H  Q   V  K  I  C  D  F  G 1630                    1650                    1670
                 .                       .                       .
GCAGTGCGAAACAGCTCGTAAGACTTTGTGACATATAAACTCATTGGACTTGTAGCGGTT
CGTCACGCTTTGTCGAGCATTCTGAAACACTGTATATTTGAGTAAGCTGAACATCGCCAA
```

FIG. 1C

```
          S   A   K   Q   L 1690                1710                1730
              .                   .                   .
     GTTGTTTTCTGTGATCTTGTCATTTACTGTTGAAATCTACTTTTGCTTCAGGTTAAAGGT
     CAACAAAAGACACTAGAACAGTAAATGACAACTTTAGATGAAAACGAAGTCCAATTTCCA
                                                              V   K   G

120f3
            1750                1770                1790
              .                   .                   .
     GAAGCCAACATTTCTTACATCTGCTCACGATTCTAC CGTGCACC CGAGCTCATATTTGGT
     CTTCGGTTGTAAAGAATGTAGACGAGTGCTAAGATG GCA(6)GTGG GCTCGAGTATAAACCA
      E   A   N   I   S   Y   I   C   S   R   F   Y  R   P   E   L   I   F   G 1810                1830                1850
              .                   .                   .
     GCCACTGAGTACACAACTTCTATTGATATCTGGTCTGCTGGTTGTGTTCTTGCTGAGCTT
     CGGTGACTCATGTGTTGAAGATAACTATAGACCAGACGACCAACACAAGAACGACTCGAA
      A   T   E   Y   T   T   S   I   D   I   W   S   A   G   C   V   L   A   E   L 1870                1890                1910
              .                   .                   .
     CTTCTTGGTCAGGTAAACAATTCTTTCAGTAACCAGCTTATTCAATCTCCATGTGTATAT
     GAAGAACCAGTCCATTTGTTAAGAAAGTCATTGGTCGAATAAGTTAGAGGTACACATATA
      L   L   G   Q 1930                1950                1970
              .                   .                   .
     TTGCATTAGGACTCATTGTGACTATATCATGTTCTTATGCAGCCAT TATT(7)CCC GGAGAA
     AACGTAATCCTGAGTAACACTGATATAGTACAAGAATACGTCGGTA ATAA AGGG CCTCTT
                                                  P   L   F   P   G   E 1990                2010                2030
              .                   .                   .
     AATGCTGTGGATCAGCTCGTTGAAATTATAAAAGTAAGAATCTTTAAACGATGATTCCTT
     TTACGACACCTAGTCGAGCAACTTTAATATTTTCATTCTTAGAAATTTGCTACTAAGGAA
      N   A   V   D   Q   L   V   E   I   I   K

120f5
            2050                2070                2090
              .                   .                   .
     GCAAATTACATTCTTTGGCTACAAAATCCTCACTGTATAGTTGTTGTACACAGGTTCTTG
     CGTTTAATGTAAGAAACCGATGTTTTAGGAGTGACATATCAACAACATGTGTCCAAGAAC
                                                              V   L   G 2110                2130                2150
              .                   .                   .
     GTACACCAACTCGAGAAGAAATCCGTTGTATGAATC CAC(8)TTAC ACAGATTTCAGGTTTC
     CATGTGGTTGAGCTCTTCTTTAGGCAACATACTTAG GTG AATG TGTCTAAAGTCCAAAG
      T   P   T   R   E   E   I   R   C   M   N   P  H   Y   T   D   F   R   F
                   K in dwf12-1 (wm1-1)
                   K in dwf12-2 (wm5-1)

```
CACAGATAAAGGCACATCCCTGGCACAAGGTTAGTGTCTTTTCTCTTTTTGCATGTGTTC
GTGTCTATTTCCGTGTAGGGACCGTGTTCCAATCACAGAAAAGAGAAAAACGTACACAAG
  Q  I  K  A  H  P  W  H  K 2230              2250              2270
                 .                 .                 .
TTGTTTCAGTTTCTTTCTTCACACATCAACTGATCATAATTACGTTTTGGTTTAGATCTT
AACAAAGTCAAAGAAAGAAGTGTGTAGTTGACTAGTATTAATGCAAAACCAAATCTAGAA
                                                         I  F 2290              2310              2330
                 .                 .                 .
CCACAAAAGGATGCCCCCAGAAGCGATTGATTTTGCATCAAGGCTGCTTCAATACTCTCC
GGTGTTTTCCTACGGGGGTCTTCGCTAACTAAAACGTAGTTCCGACGAAGTTATGAGAGG
  H  K  R  M  P  P  E  A  I  D  F  A  S  R  L  L  Q  Y  S  P
                                  ┌─────────┐
                                  │ 9       │
                                  └─────────┘

2350              2370              2390
                 .                 .                 .
AAGTCTAAGATGCACAGCGGTAAGCATTGGTCTTGAGGTTTCTTCAGTCTCTAAGAATCC
TTCAGATTCTACGTGTCGCCATTCGTAACCAGAACTCCAAAGAAGTCAGAGATTCTTAGG
  S  L  R  C  T  A 2410              2430              2450
                 .                 .                 .
AACTGAATCCTTACTATATATTTTGTTTCCTCGTATTTCAGCTCGAAGCTTGTGCACATC
TTGACTTAGGAATGATATATAAAACAAAGGAGCATAAAGTCGAGCTTCGAACACGTGTAG
                                         L  E  A  C  A  H  P 2470              2490              2510
                 .                 .                 .
CGTTCTTTGATGAACTCAGAGAACCAAACGCTCGTTTACCAAATGGACGGCCTTTCCCGC
GCAAGAAACTACTTGAGTCTCTTGGTTTGCGAGCAAATGGTTTACCTGCCGGAAAGGGCG
  F  F  D  E  L  R  E  P  N  A  R  L  P  N  G  R  P  F  P  P
                                         ┌─────────┐
                                         │ 10      │
                                         └─────────┘

2530              2550              2570
                 .                 .                 .
CTCTCTTCAACTTCAAACAAGAAGTAGCTGGATCATCACCTGAACTGGTCAACAAGTTGA
GAGAGAAGTTGAAGTTTGTTCTTCATCGACCTAGTAGTGGACTTGACCAGTTGTTCAACT
  L  F  N  F  K  Q  E  V  A  G  S  S  P  E  L  V  N  K  L  I 2590              2610              2630
                 .                 .                 .
TTCCAGACCATATCAAGAGACAATTGGGTCTAAGCTTCTTGAATCAATCTGGAACTTAAA
AAGGTCTGGTATAGTTCTCTGTTAACCCAGATTCGAAGAACTTAGTTAGACCTTGAATTT
  P  D  H  I  K  R  Q  L  G  L  S  F  L  N  Q  S  G  T  *

2590              2610              2630
                 .                 .                 .
TTCCAGACCATATCAAGAGACAATTGGGTCTAAGCTTCTTGAATCAATCTGGAACTTAAA
AAGGTCTGGTATAGTTCTCTGTTAACCCAGATTCGAAGAA<u>CTTAGTTAGACCTTGAATTT</u>
  P  D  H  I  K  R  Q  L  G  L  S  F  L  N  Q  S  G  T  *

D12-OVR1
              2650              2670              2690
tctaga            <u>T</u>          <u>GA</u>
```

FIG. 1E

AGGGATCCTGCAAAAGACAACTACTTTTTTATATATAATGTACCATTACACGAGCCACAA
TCCCagatctctgTTCTGTaGATctAAAAATATATATTACATGGTAATGTGCTCGGTGTT AGGGATCCTGCAAAAGACAACTACTTTTTTATATATAATGTACCATTACACGAGCCACAA
TCCCTAGGACGTTTTCTGTTGATGAAAAAATATATATTACATGGTAATGTGCTCGGTGTT 2710                 2730                 2750

GGTCGTAGTTGAAGGCAAACGTGGAGGACACAATTCAAAGTTTTTCCTCCTCAAACTCGT
CCAGCATCAACTTCCGTTTGCACCTCCTGTGTTAAGTTTCAAAAAGGAGGAGTTTGAGCA

2770

TCAGACAAAGCCAGCTGCTAGCAAAAC
AGTCTGTTTCGGTCGACGATCGTTTTG

*FIG. 1F* cDNA sequences

```
AGAAAGAGAAAGAGAAGAGCTGGATTCACATGGTCTTGTTCTTTCTCTCTCCTTCTTTTCTCATCTTGCGGCTTCCCT
TTCTCTCTCTATCGCCACAATGATCATTACCAACCAAACTGATTGAAACTCATTTGTTCTCTCTCTCTCAAATCCACTCT
CTCTCTTTCTTTTCTCTTCTCCTCTCTGTGTCTCTATCGCCATGGCTGATGATAAGGAGATGCCTGCTGCTGTAGTTGAT
GGACATGATCAAGTCACTGGTCATATTATTTCCACCACAATCGGTGGCAAAAATGGTGAACCAAAACAGACAATTAGTTA
CATGGCGGAGCGAGTTGTTGGTACAGGCTCGTTCGGGATCGTTTTCCAAGCAAAATGTTTGGAGACTGGAGAAACCGTGG
CGATAAAGAAGGTTTTGCAAGATAGAAGATACAAGAACCGAGAACTTCAGTTGATGCGTGTGATGGATCATCCGAATGTG
GTTTGTTTGAAGCATTGCTTCTTTTCGACTACAAGTAAAGACGAGCTTTTCTTGAACTTGGTTATGGAGTATGTCCCTGA
GAGCTTGTATCGAGTTCTGAAACATTATAGTAGTGCAAACCAAAGAATGCCTCTTGTCTATGTTAAACTTTACATGTATC
AGATCTTCCGGGGACTTGCTTACATTCACAATGTTGCTGGAGTTTGTCACAGAGATCTAAAGCCTCAAAATCTTCTGGTT
GATCCTCTTACTCATCAAGTCAAAATCTGTGACTTTGGCAGTGCGAAACAGCTCGTTAAAGGTGAAGCCAACATTTCTTA
CATCTGCTCACGATTCTACCGTGCACCCGAGCTCATATTTGGTGCCACTGAGTACACAACTTCTATTGATATCTGGTCTG
CTGGTTGTGTTCTTGCTGAGCTTCTTCTTGGTCAGCCATTATTTCCCGGAGAAAATGCTGTGGATCAGCTCGTTGAAATT
ATAAAAGTTCTTGGTACACCAACTCGAGAAGAAATCCGTTGTATGAATCCACATTACACAGATTTCAGGTTTCCACAGAT
AAAGGCACATCCCTGGCACAAGATCTTCCACAAAAGGATGCCCCCAGAAGCGATTGATTTTGCATCAAGGCTGCTTCAAT
ACTCTCCAAGTCTAAGATGCACAGCGCTCGAAGCTTGTGCACATCCGTTCTTTGATGAACTCAGAGAACCAAACGCTCGT
TTACCAAATGGACGGCCTTTCCCGCCTCTCTTCAACTTCAAACAAGAAGTAGCTGGATCATCACCTGAACTGGTCAACAA
GTTGATTCCAGACCATATCAAGAGACAATTGGGTCTAAGCTTCTTGAATCAATCTGGAACTTAAAAGGGATCCTGCAAAA
GACAACTACTTTTTTATATATAATGTACCATTACACGAGCCACAAGGTCGTAGTTGAAGGCAAACGTGGAGGACACAATT
CAAAGTTTTTCCTCCTCAAACTCGTTCAGACAAAGCCAGCTGCTAGCAAAAC
```

FIG. 2

```
            10                    30                    50
             .                     .                     .
MADDKEMPAAVVDGHDQVTGHIISTTIGGKNGEPKQTISYMAERVVGTGSFGIVFQAKCL
                                              PK_ATP predicted
                                              by annotation 70                    90                   110
             .                     .                     .
ETGETVAIKKVLQDRRYKNRELQLMRVMDHPNVVCLKHCFFSTTSKDELFLNLVMEYVPE
         PS00007 TYR_PHOSPHO_SITE          PS00005 PKC_PHOSPHO_SITE
                                           PS00006 CK2_PHOSPHO_SITE 130                   150                   170
             .                     .                     .
SLYRVLKHYSSANQRMPLVYVKLYMYQIFRGLAYIHNVAGVCHRDLKPQNLLVDPLTHQV
                                   IPB000719A Euk PK-domain: ATP binding
                                              P_K_St pred. by ann.

190                   210                   230
             .                     .                     .
KICDFGSAKQLVKGEANISYICSRFYRAPELIFGATEYTTSIDIWSAGCVLAELLLGQPL
    PS00005 PKC_PHOSPHO_SITE            PS00006 CK2_PHOSPHO_SITE
             PS00001 ASN_GLYCOSYLATION
                                     IPB000719B Euk PK-domain: Subst.
                                                binding
           250                   270                   290
             .                     .                     .
FPGENAVDQLVEIIKVLGTPTREEIRCMNPHYTDFRFPQIKAHPWHKIFHKRMPPEAIDF
                    || E264K dwf12-1 (wm1-1)
                    |  E263K dwf12-2 (wm5-1)
                 PS00006 CK2_PHOSPHO_SITE 310                   330                   350
             .                     .                     .
ASRLLQYSPSLRCTALEACAHPFFDELREPNARLPNGRPFPPLFNFKQEVAGSSPELVNK
         PS00005 PKC_PHOSPHO_SITE          PS00006 CK2_PHOSPHO_SITE
           PS00006 CK2_PHOSPHO_SITE
           PR01049B PK Domain signature

370
             .
LIPDHIKRQLGLSFLNQSGT
         PS00001 ASN_GLYCOSYLATION
```

FIG. 3

DWF12 AND MUTANTS THEREOF

CROSS REFERENCE TO RELATED APPLICATIONS

This application is a National Stage Application under 35 U.S.C. § 371 that claims the benefit of PCT/U502/15563, filed May 15, 2002; which claims the benefit of U.S. Provisional Application Ser. No. 60/291,342, filed May 16, 2001, both of which are incorporated by reference in their entirety for all purposes.

TECHNICAL FIELD

The present invention relates generally to plants that display altered biochemical properties, structure or morphology and to the genes imparting such phenotypes. In particular, the present invention pertains to DWARF12 (DWF12), dwf12 mutants and methods of using the same.

BACKGROUND OF THE INVENTION

The brassinosteroids (BRs) are a group of plant steroid hormones that help regulate many different aspects of plant growth and development. BRs are known to stimulate cell elongation and division, and are also involved in vascular system differentiation, reproduction, and stress responses (Altmann, 1998; Clouse and Sasse, 1998). Recently, it has been shown that mutants defective either in BR biosynthesis or signaling, display altered developmental phenotypes including dwarfism, reduced fertility, and abnormal vasculature (Clouse and Feldmann, 1999).

BR dwarf mutants can be divided into two classes. The first class of mutants is perturbed in BR signaling. For example, Clouse, et al., (1996) isolated a signaling mutant, brassinosteroid insensitive1 (bri1), that was resistant to exogenously applied BRs. BRI1 has been cloned and shown to encode a leucine-rich repeat receptor kinase, suggesting a role for BR perception at the cellular membrane (Li and Chory, 1997). Recently, it was demonstrated that bri1 mutants accumulate significant amounts of brassinolide (BL) and its precursors compared to wild-type controls, suggesting that perception is coupled to homeostasis of endogenous BR levels (Noguchi, et al., 1999b).

The other class of BR mutants includes a large number of dwarfs that are defective in BR biosynthesis. Plants produce BRs using sterols as precursors, and the sterol biosynthetic pathway uses mevalonic acid as a precursor to synthesize sterols, such as sitosterol, stigmasterol, and campesterol. Sterols are modified by the BR-specific pathway to produce the end product, BL, and its congeners. Thus, mutants that are defective in either the sterol or BR-specific pathway display a typical BR dwarf phenotype, and can be rescued to a wild-type phenotype by exogenous application of BRs.

The characteristic phenotype of BR dwarf mutants has been instrumental in isolating additional mutants, and their corresponding genes perturbed in the complex plant sterol biosynthesis network. dwf1 was the first mutant isolated to have this dwarf phenotype (Feldmann, et al., 1989). The dwf1 mutant is defective in C-24 reduction, and DWF1 encodes a FAD-binding oxidoreductase (Choe, et al., 1999a; Klahre, et al., 1998; Takahashi, et al., 1995). The pea lkb mutant is deficient in the same reaction as *Arabidopsis* dwf1 (Nomura, et al., 1999). Another sterol mutant, *Arabidopsis* dwf7/ste1, has been isolated and found to be defective in the $\Delta^7$ sterol C-5 desaturase gene (Gachotte, et al., 1995; 1996; Husselstein, et al., 1999, Choe, et al., 1999b).

Currently, little is known about the downstream events that occur in response to signals in the above pathways that ultimately control cell size. This is because the biochemical and cell biological processes involved have thus far been difficult to address. In addition, there is little information about the integration of regulatory signals converging at the cell from different signaling pathways and the ways they are coordinately controlled. In particular, the interaction of light and hormones in the control of cell elongation is not clear. Thus, there remains a need for the identification and characterization of additional mutants, and polypeptides encoded thereby, of enzymes involved in these pathways of plant growth.

Eukaryotic protein kinases are an extensive family of enzymes, many of which mediate the response of eukaryotic cells to external stimuli. One type of protein kinase, known as "SHAGGY," is widespread in the plant kingdom and is a serine/threonine protein kinase which is homologous to the mammalian glycogen synthase kinase-3 (GSK-3). Plant homologs of GSK-3 have been found in such divergent plant species as *Arabidopsis* (Bianchi et al., *Mol. Gen. Genet.* (1994) 242:337-345; Jonak et al., *Plant. Mol. Biol.* (1995) 27:217-221; Dornelas et al., *Plant Physiol.* (1997) 113:306) *Medicago* (Pay et al., *Plant J.* (1993) 3:847-856), *Nicotiana* (Elinzenberger et al., *Biochem. Biophys. Acta* (1995) 1260: 315-319); and *Petunia* (Decroocq-Ferrant et al., *Plant J.* (1995) 7:897-911), among others. Despite the widespread occurrence of SHAGGY protein kinases in higher plants, very little is known about the role these proteins play in plant development.

SUMMARY OF THE INVENTION

The present invention is based on the discovery of various mutants in a BR signaling pathway featuring the kinase designated DWARF12 (DWF12) herein. The DWF12 protein has been characterized as a SHAGGY protein kinase. dwf12 mutants are phenotypically similar to other reported BR mutants, displaying phenotypes such as short stature, short round leaves, reduced fertility and fecundity, and abnormal de-etiolation. dwf12 mutants also have a unique phenotype, severe downward curling of leaves. Without being bound by a particular theory, DWF12 appears to act downstream of BRI in a phosphorylation cascade, ultimately leading to the activation of BR-dependent transcriptional events.

Accordingly, in one embodiment, the present invention is directed to an isolated dwf12 mutant polypeptide with at least about 70% sequence identity to the polypeptide depicted at positions 38-326 or 1-380 of FIG. 3, wherein said polypeptide comprises a mutation comprising at least one non-conservative substitution, addition or deletion of an amino acid in a region of the polypeptide depicted in FIG. 3, wherein said region is one or more of (a) a casein kinase II phosphorylation domain spanning positions 104-106 of FIG. 3; (b) a casein kinase II phosphorylation domain spanning positions 220-223 of FIG. 3; (c) a casein kinase II phosphorylation domain spanning positions 261-264 of FIG. 3; (d) a casein kinase II phosphorylation domain spanning positions 314-317 of FIG. 3; (e) a casein kinase II phosphorylation domain spanning positions 353-356 (f) a protein kinase C phosphorylation domain spanning positions 104-106 of FIG. 3; (g) a protein kinase C phosphorylation domain spanning positions 187-189 of FIG. 3; (h) a protein kinase C phosphorylation domain spanning positions 310-312; (i) the active site lysine residue found at position 69 of FIG. 3; (j) a tyrosine phosphorylation domain spanning positions 70-77 of FIG. 3; (k) a protein kinase ATP-binding domain spanning positions 46-69 of FIG. 3; (l) a eukaryotic protein kinase ATP-binding domain spanning positions 157-172 of FIG. 3; (m) a eukaryotic protein kinase substrate-binding domain spanning positions 218-228 of FIG. 3; (n) a eukaryotic protein kinase signature sequence spanning positions 316-327 of FIG. 3; (o) a glycosylation domain spanning positions 197-200 of FIG. 3; or (p) a glycosylation domain spanning positions 376-379 of FIG. 3. Additionally, the mutation may occur within the sequence CDFGSAK, found at positions 183-189 of FIG. 3, as well as the sequence SYICSR, found at positions 199-204 of FIG. 3.

Alternatively, the isolated dwf12 mutant polypeptide has at least about 70% sequence identity to a polypeptide designated in Table 1, and has one or more mutations in a domain corresponding to the domains set forth above.

In certain embodiments, the mutation comprises a change in a casein kinase II phosphorylation domain as specified above of an acidic amino acid residue such as Asp or Glu, to a basic amino acid residue, such as Lys, Arg or His. In other embodiments, the mutation comprises a change in a protein kinase C phosphorylation domain as specified above of a basic amino acid residue to an acidic amino acid residue.

In additional embodiments, the mutation comprises a mutation to the sequence spanning positions 261-264 of FIG. 3, such as a change of Glu-263, or Glu-264, to Lys.

In another embodiment, the present invention is directed to an isolated dwf12 mutant polynucleotide which encodes a polypeptide as specified above. In certain embodiments, the polynucleotide is (a) a dwf12-1 polynucleotide comprising the dwf12-1 nucleotide sequence depicted in FIGS. 1A-1F; or (b) a dwf12-2 polynucleotide comprising the dwf12-2 nucleotide sequence depicted in FIGS. 1A-1F.

In certain embodiments, the isolated polynucleotide imparts at least one dwf12 mutant phenotype when expressed in a plant.

The altered phenotype may be any microscopic or macroscopic change in structure or morphology, as well as biochemical differences, which are characteristic of a dwf12 plant, as compared to a progenitor, wild-type plant cultivated under the same conditions. Biochemical differences include reduced or increased SHAGGY kinase activity as compared to the wild-type polypeptide. Reduced activity, for example, may in turn result an accumulation of significant amounts of BRs, such as brassinolide. Generally, morphological differences include a short robust stature, short internodes, an increased number of inflorescences, and small dark-green, round leaves. Particularly unique to dwf12 plants is the presence of severe downward curling of leaves. Moreover, plants may have short siliques and be infertile.

In a further embodiment, the invention is directed to a recombinant vector comprising (i) a polynucleotide as described above; and (ii) control elements operably linked to said polynucleotide whereby a coding sequence within said polynucleotide can be transcribed and translated in a host cell, as well as host cells comprising the vector.

In still further embodiments, the invention is directed to a method of producing a recombinant polypeptide comprising:

(a) providing a host cell as specified above; and
(b) culturing said host cell under conditions whereby a recombinant polypeptide encoded by the coding sequence present in said recombinant vector is expressed.

In another embodiment, the invention is directed to a transgenic plant comprising a dwf12 mutant polynucleotide, wherein said mutant polynucleotide encodes for a dwf12 mutant polypeptide having a mutation as described above. In certain embodiments, the dwf12 polynucleotide is dwf12-1 or dwf12-2, described above.

In still another embodiment, the invention is directed to a method of producing a transgenic plant comprising:

(a) introducing a dwf12 mutant polynucleotide, or a recombinant vector, as described above, into a plant cell to produce a transformed plant cell; and
(b) producing a transgenic plant from the transformed plant cell.

In another embodiment, the invention is directed to a method for producing a transgenic plant having an altered phenotype relative to the corresponding wild-type plant comprising:

(a) introducing a dwf12 mutant polynucleotide, or recombinant vector as described above into a plant cell; and
(b) producing a transgenic plant from the plant cell, said transgenic plant having an altered phenotype relative to the corresponding wild-type plant.

In certain embodiments, the polynucleotide is operably linked to a promoter selected from the group consisting of a tissue-specific promoter, an inducible promoter and a constitutive promoter. Additionally, the polynucleotide may be overexpressed or may inhibit expression of DWF12. Additionally, the method may be one wherein at least first and second polynucleotides are introduced into the plant cell, said first and second polynucleotides operably linked to at least first and second tissue-specific promoters, wherein said first polynucleotide is overexpressed and said second polynucleotide inhibits expression of DWF12.

In still further embodiments, the invention is directed to a method of modulating an endogenous DWF12 polypeptide in a transgenic plant, and hence SHAGGY kinase activity, said method comprising providing a polynucleotide as described above. The polynucleotide may be overexpressed or expression of the polynucleotide may be inhibited.

In another embodiment the invention is directed a method for altering the biochemical activity, such as SHAGGY kinase activity, of a cell comprising:

(a) introducing at least one polynucleotide as described above into the cell; and
(b) causing expression of said polynucleotide such that the biochemical activity of the cell is altered. The polynucleotide may be introduced into the cell ex vivo or in vivo.

Additionally, more than one dwf12 polynucleotide may be provided to the cell.

In yet a further embodiment, the subject invention is directed to a method for modulating a trait in a plant, wherein said trait is selected from the group consisting of (a) biomass; (b) height; (c) tissue or organ size, such as but not limited to leaf, seed, root, flower, stem, petioles, internodes, hypocotyl size; (d) fertility; (e) fecundity; (f) leaf curling, including the rosette and/or cauline; (g) cell elongation; and (h) stress tolerance.

In certain embodiments, the trait is modulated by modulating expression of an endogenous SHAGGY kinase by inserting a polynucleotide into a cell wherein said polynucleotide encodes for a SHAGGY kinase exhibiting reduced activity as compared to the corresponding endogenous SHAGGY kinase, such as a polynucleotide that encodes a mutant dwf12 polypeptide with reduced activity. Alternatively, the mutant dwf12 polypeptide may have enhanced activity, e.g., due to mutations in, for example, a phosphorylation site. The polynucleotide may be heterologous to the cell, i.e., it may be derived from a different plant species than the cell, and/or the polynucleotide may comprise multiple copies of the mutant SHAGGY kinase. The SHAGGY kinase modulated is preferably one involved in a BR signaling pathway, such as DWF12 or a homologue thereof. The polynucleotide may also encode a SHAGGY kinase exhibiting at least the same or enhanced activity as compared to the corresponding endogenous SHAGGY kinase, such as a polynucleotide that encodes a mutant dwf12 polypeptide with enhanced activity or a homologue thereof. Moreover, the polynucleotide may be one that is capable of hybridizing to the endogenous SHAGGY kinase mRNA. The polynucleotide may be a mutant dwf12 polynucleotide as specified above.

These and other embodiments of the present invention will readily occur to those of ordinary skill in the art in view of the disclosure herein.

BRIEF DESCRIPTION OF THE FIGURES

FIGS. 1A-1F present the genomic sequence of the DWF12 locus (SEQ ID NO:1), showing the various exons (those regions with amino acid sequences depicted below the nucleotide sequence and with numbered boxes 1-10 (SEQ ID NO:2-11, respectively)), and introns (no corresponding polypeptide sequence indicated), and sites of mutations corresponding to dwf12-2 and dwf12-2.

FIG. 2 shows a sequence of a DWFJ2 cDNA (SEQ ID NO:12).

FIG. 3 shows the amino acid sequence of DWF12 (SEQ ID NO:13). The dwf12-1 mutant polypeptide has a substitution of Lys for Glu at position 264 of FIG. 3, and the dwf12-2 mutant polypeptide includes a substitution of Lys for Glu at position 263 of FIG. 3. Also indicated in the figure are the casein kinase II phosphorylation domains (designated as "CK2_PHOSPHO_SITE"); the protein kinase C phosphorylation domains (designated as "PKC_PHOSPHO_SITE"); the tyrosine phosphorylation domain (designated as "TYR_PHOSPHO_SITE"); the phosphokinase domain signature (designated "PK Domain signature); and the asparagine glycosylation sites.

DETAILED DESCRIPTION OF THE INVENTION

The practice of the present invention will employ, unless otherwise indicated, conventional methods of protein chemistry, biochemistry, recombinant DNA techniques and pharmacology, within the skill of the art. Such techniques are explained fully in the literature. See, e.g., Evans, et al., *Handbook of Plant Cell Culture* (1983, Macmillan Publishing Co.); Binding, *Regeneration of Plants, Plant Protoplasts* (1985, CRC Press); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences*, 18th Edition (Easton, Pa.: Mack Publishing Company, 1990).

All publications, patents and patent applications cited herein, whether supra or infra, are hereby incorporated by reference in their entirety.

It must be noted that, as used in this specification and the appended claims, the singular forms "a", "an" and "the" include plural referents unless the content clearly dictates otherwise. Thus, for example, reference to "a polypeptide" includes a mixture of two or more polypeptides, and the like.

The following amino acid abbreviations are used throughout the text:

| | |
|---|---|
| Alanine: Ala (A) | Arginine: Arg (R) |
| Asparagine: Asn (N) | Aspartic acid: Asp (D) |
| Cysteine: Cys (C) | Glutamine: Gln (Q) |
| Glutamic acid: Glu (E) | Glycine: Gly (G) |
| Histidine: His (H) | Isoleucine: Ile (I) |
| Leucine: Leu (L) | Lysine: Lys (K) |
| Methionine: Met (M) | Phenylalanine: Phe (F) |
| Proline: Pro (P) | Serine: Ser (S) |
| Threonine: Thr (T) | Tryptophan: Trp (W) |
| Tyrosine: Tyr (Y) | Valine: Val (V) |

The following conventions are followed herein with respect to DWF12:

DWF12 denotes a wild-type protein sequence;

dwf12 denotes a protein sequence which deviates from the wild-type sequence;

DWF12 denotes the wild-type polynucleotide sequence;

dwf12 denotes a polynucleotide that deviates from the wild-type sequence.

I. Definitions

In describing the present invention, the following terms will be employed, and are intended to be defined as indicated below.

The terms "nucleic acid molecule" and "polynucleotide" are used interchangeably and refer to a polymeric form of nucleotides of any length, either deoxyribonucleotides or ribonucleotides, or analogs thereof. This term refers only to the primary structure of the molecule and thus includes double- and single-stranded DNA and RNA. It also includes known types of modifications, for example, labels which are known in the art, methylation, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example proteins (including e.g., nucleases, toxins, antibodies, signal peptides, poly-L-lysine, etc.), those with intercalators (e.g., acridine, psoralen, etc.), those containing chelates (e.g., metals, radioactive metals, boron, oxidative metals, etc.), those containing alkylators, those with modified linkages (e.g., alpha anomeric nucleic acids, etc.), as well as unmodified forms of the polynucleotide. Polynucleotides may have any three-dimensional structure, and may perform any function, known or unknown. Nonlimiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term polynucleotide sequence is the alphabetical representation of a polynucleotide molecule. This alphabetical representation can be input into databases in a computer having a central processing unit and used for bioinformatics applications such as functional genomics and homology searching.

Techniques for determining nucleic acid and amino acid "sequence identity" are known in the art. Typically, such techniques include determining the nucleotide sequence of the mRNA for a gene and/or determining the amino acid sequence encoded thereby, and comparing these sequences to a second nucleotide or amino acid sequence. In general, "identity" refers to an exact nucleotide-to-nucleotide or amino acid-to-amino acid correspondence of two polynucleotides or polypeptide sequences, respectively. Two or more sequences (polynucleotide or amino acid) can be compared by determining their "percent identity." The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, *Advances in Applied Mathematics* 2:482-489 (1981). This algorithm can be applied to amino acid sequences by using the scoring matrix developed by Dayhoff, *Atlas of Protein Sequences and Structure*, M. O. Dayhoff ed., 5 suppl. 3:353-358, National Biomedical Research Foundation, Washington, D.C., USA, and normalized by Gribskov, *Nucl. Acids Res.* 14(6):6745-6763 (1986). An exemplary implementation of this algorithm to determine percent identity of a sequence is provided by the Genetics Computer Group (Madison, Wis.) in the "BestFit" utility application. The default parameters for this method are described in the Wisconsin Sequence Analysis Package Program Manual, Version 8 (1995) (available from Genetics Computer Group, Madison, Wis.). A preferred method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found at the following internet address: http://www.ncbi.nlm.gov/cgi-bin/BLAST.

Alternatively, the degree of sequence similarity between polynucleotides can be determined by hybridization of polynucleotides under conditions that form stable duplexes between homologous regions, followed by digestion with single-stranded-specific nuclease(s), and size determination of the digested fragments. Two DNA, or two polypeptide sequences are "substantially homologous" to each other when the sequences exhibit at least about 70%-85%, preferably at least about 85%-90%, more preferably at least about 90%-95%, and most preferably at least about 95%-98% sequence identity over a defined length of the molecules, or any percentage between the above-specified ranges, as determined using the methods above. As used herein, substantially homologous also refers to sequences showing complete identity to the specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning*, supra; *Nucleic Acid Hybridization*, supra.

The degree of sequence identity between two nucleic acid molecules affects the efficiency and strength of hybridization events between such molecules. A partially identical nucleic acid sequence will at least partially inhibit a completely identical sequence from hybridizing to a target molecule. Inhibition of hybridization of the completely identical sequence can be assessed using hybridization assays that are well known in the art (e.g., Southern blot, Northern blot, solution hybridization, or the like, see Sambrook, et al., *Molecular Cloning: A Laboratory Manual*, Second Edition, (1989) Cold Spring Harbor, N.Y.). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a target nucleic acid sequence, and then by selection of appropriate conditions the probe and the target sequence "selectively hybridize," or bind, to each other to form a hybrid molecule. A nucleic acid molecule that is capable of hybridizing selectively to a target sequence under "moderately stringent" typically hybridizes under conditions that allow detection of a target nucleic acid sequence of at least about 10-14 nucleotides in length having at least approximately 70% sequence identity with the sequence of the selected nucleic acid probe. Stringent hybridization conditions typically allow detection of target nucleic acid sequences of at least about 10-14 nucleotides in length having a sequence identity of greater than about 90-95% with the sequence of the selected nucleic acid probe. Hybridization conditions useful for probe/target hybridization where the probe and target have a specific degree of sequence identity, can be determined as is known in the art (see, for example, *Nucleic Acid Hybridization: A Practical Approach* editors B. D. Hames and S. J. Higgins, (1985) Oxford; Washington, D.C.; IRL Press).

With respect to stringency conditions for hybridization, it is well known in the art that numerous equivalent conditions can be employed to establish a particular stringency by varying, for example, the following factors: the length and nature of probe and target sequences, base composition of the various sequences, concentrations of salts and other hybridization solution components, the presence or absence of blocking agents in the hybridization solutions (e.g., formamide, dextran sulfate, and polyethylene glycol), hybridization reaction temperature and time parameters, as well as, varying wash conditions. The selection of a particular set of hybridization conditions is selected following standard methods in the art (see, for example, Sambrook, et al., *Molecular Cloning: A Laboratory Manual*, Second Edition, (1989) Cold Spring Harbor, N.Y.).

A "gene" as used in the context of the present invention is a sequence of nucleotides in a genetic nucleic acid (chromosome, plasmid, etc.) with which a genetic function is associated. A gene is a hereditary unit, for example of an organism, comprising a polynucleotide sequence that occupies a specific physical location (a "gene locus" or "genetic locus") within the genome of an organism. A gene can encode an expressed product, such as a polypeptide or a polynucleotide (e.g., tRNA). Alternatively, a gene may define a genomic location for a particular event/function, such as the binding of proteins and/or nucleic acids, wherein the gene does not encode an expressed product. Typically, a gene includes coding sequences, such as, polypeptide encoding sequences, and non-coding sequences, such as, promoter sequences, polyadenlyation sequences, transcriptional regulatory sequences (e.g., enhancer sequences). Many eucaryotic genes have "exons" (coding sequences) interrupted by "introns" (non-coding sequences). In certain cases, a gene may share sequences with another gene(s) (e.g., overlapping genes).

A "coding sequence," or a sequence which "encodes" a selected polypeptide, is a nucleic acid molecule which is transcribed (in the case of DNA) and translated (in the case of mRNA) into a polypeptide, for example, in vivo when placed under the control of appropriate regulatory sequences (or "control elements"). The boundaries of the coding sequence are typically determined by a start codon at the 5' (amino) terminus and a translation stop codon at the 3' (carboxy) terminus. A coding sequence can include, but is not limited to, cDNA from viral, procaryotic or eucaryotic mRNA, genomic DNA sequences from viral or procaryotic DNA, and even synthetic DNA sequences. A transcription termination sequence may be located 3' to the coding sequence. Other "control elements" may also be associated with a coding sequence. A DNA sequence encoding a polypeptide can be optimized for expression in a selected cell by using the codons preferred by the selected cell to represent the DNA copy of the desired polypeptide coding sequence. "Encoded by" refers to a nucleic acid sequence which codes for a polypeptide sequence, wherein the polypeptide sequence or a portion thereof contains an amino acid sequence of at least 3 to 5 amino acids, more preferably at least 8 to 10 amino acids, and even more preferably at least 15 to 20 amino acids from a polypeptide encoded by the nucleic acid sequence. Also encompassed are polypeptide sequences which are immunologically identifiable with a polypeptide encoded by the sequence.

Typical "control elements", include, but are not limited to, transcription promoters, transcription enhancer elements, transcription termination signals, polyadenylation sequences (located 3' to the translation stop codon), sequences for optimization of initiation of translation (located 5' to the coding sequence), translation enhancing sequences, and translation termination sequences. Transcription promoters can include inducible promoters (where expression of a polynucleotide sequence operably linked to the promoter is induced by a cofactor, regulatory protein, etc.), repressible promoters (where expression of a polynucleotide sequence operably linked to the promoter is induced by a cofactor, regulatory protein, etc.), and constitutive promoters.

A control element, such as a promoter, "directs the transcription" of a coding sequence in a cell when RNA polymerase will bind the promoter and transcribe the coding sequence into mRNA, which is then translated into the polypeptide encoded by the coding sequence.

"Expression enhancing sequences" typically refer to control elements that improve transcription or translation of a polynucleotide relative to the expression level in the absence of such control elements (for example, promoters, promoter enhancers, enhancer elements, and translational enhancers (e.g., Shine and Delagamo sequences).

"Operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences. The control elements need not be contiguous with the coding sequence, so long as they function to direct the expression thereof. Thus, for example, intervening untranslated yet transcribed sequences can be present between a promoter and the coding sequence and the promoter can still be considered "operably linked" to the coding sequence.

A "heterologous sequence" as used herein typically refers to a nucleic acid sequence that is not normally found in the cell or organism of interest. For example, a DNA sequence encoding a polypeptide can be obtained from a plant cell and introduced into a bacterial cell. In this case the plant DNA sequence is "heterologous" to the native DNA of the bacterial cell.

The "native sequence" or "wild-type sequence" of a gene is the polynucleotide sequence that comprises the genetic locus corresponding to the gene, e.g., all regulatory and open-reading frame coding sequences required for expression of a completely functional gene product as they are present in the wild-type genome of an organism. The native sequence of a gene can include, for example, transcriptional promoter sequences, translation enhancing sequences, introns, exons, and poly-A processing signal sites. It is noted that in the general population, wild-type genes may include multiple prevalent versions that contain alterations in sequence relative to each other and yet do not cause a discernible pathological effect. These variations are designated "polymorphisms" or "allelic variations."

"Recombinant" as used herein to describe a nucleic acid molecule means a polynucleotide of genomic, cDNA, semi-synthetic, or synthetic origin which, by virtue of its origin or manipulation: (1) is not associated with all or a portion of the polynucleotide with which it is associated in nature; and/or (2) is linked to a polynucleotide other than that to which it is linked in nature. The term "recombinant" as used with respect to a protein or polypeptide means a polypeptide produced by expression of a recombinant polynucleotide.

By "vector" is meant any genetic element, such as a plasmid, phage, transposon, cosmid, chromosome, virus etc., which is capable of transferring gene sequences to target cells. Generally, a vector is capable of replication when associated with the proper control elements. Thus, the term includes cloning and expression vehicles, as well as viral vectors and integrating vectors.

As used herein, the term "expression cassette" refers to a molecule comprising at least one coding sequence operably linked to a control sequence which includes all nucleotide sequences required for the transcription of cloned copies of the coding sequence and the translation of the mRNAs in an appropriate host cell. Such expression cassettes can be used to express eukaryotic genes in a variety of hosts such as bacteria, blue-green algae, plant cells, yeast cells, insect cells and animal cells. Under the invention, expression cassettes can include, but are not limited to, cloning vectors, specifically designed plasmids, viruses or virus particles. The cassettes may further include an origin of replication for autonomous replication in host cells, selectable markers, various restriction sites, a potential for high copy number and strong promoters.

A cell has been "transformed" by an exogenous polynucleotide when the polynucleotide has been introduced inside the cell. The exogenous polynucleotide may or may not be integrated (covalently linked) into chromosomal DNA making up the genome of the cell. In procaryotes and yeasts, for example, the exogenous DNA may be maintained on an episomal element, such as a plasmid. With respect to eucaryotic cells, a stably transformed cell is one in which the exogenous DNA has become integrated into the chromosome so that it is inherited by daughter cells through chromosome replication. This stability is demonstrated by the ability of the eucaryotic cell to establish cell lines or clones comprised of a population of daughter cells containing the exogenous DNA.

"Recombinant host cells," "host cells," "cells," "cell lines," "cell cultures," and other such terms denoting procaryotic microorganisms or eucaryotic cell lines cultured as unicellular entities, are used interchangeably, and refer to cells which can be, or have been, used as recipients for recombinant vectors or other transfer DNA, and include the progeny of the original cell which has been transfected. It is understood that the progeny of a single parental cell may not necessarily be completely identical in morphology or in genomic or total DNA complement to the original parent, due to accidental or deliberate mutation. Progeny of the parental cell which are sufficiently similar to the parent to be characterized by the relevant property, such as the presence of a nucleotide sequence encoding a desired peptide, are included in the progeny intended by this definition, and are covered by the above terms.

The term "DWF12 polynucleotide" refers to a polynucleotide derived from the DWF12 genomic sequence, as depicted in FIGS. 1A-1F. The cDNA and corresponding amino acid sequences are shown in FIGS. 2 and 3, respectively. The 5' UTR is present within nucleotide positions 1-199 of FIG. 1; the coding region begins at nucleotide position 200 of FIG. 1; the downstream 3' UTR is included within nucleotide positions 2637-2787 of FIG. 1. Fragments of the sequence, as well as polynucleotide sequences homologous thereto, as defined above, and chimeras thereof, are captured by this definition. Thus, for example, a portion of the cDNA sequence shown in FIG. 2, linked to a single intron or portion of an intron from the genomic sequence, as shown in FIGS. 1A-1F, is encompassed herein.

The term "DWF12 polynucleotide" as used herein encompasses a polynucleotide derived from the sequence depicted in FIGS. 1 and/or 3, as well as modifications, fragments and chimeras thereof. The term therefore encompasses alterations to the polynucleotide sequence, so long as the alteration results in a plant displaying one or more dwf12 phenotypic traits (described below) when the polynucleotide is expressed in a plant. Such modifications typically include deletions, additions and substitutions, to the native DWF12 sequence, so long as the mutation results in a plant displaying a dwf12 phenotype as defined below. These modifications may be deliberate, as through site-directed mutagenesis, or may be accidental, such as through mutations of plants which express the DWF12 polynucleotide or errors due to PCR amplification. The term encompasses expressed allelic variants of the wild-type DWF12 sequence which may occur by normal genetic variation or are produced by genetic engineering methods and which result in a detectable change in the wild-type DWF12 phenotype. Two particular dwf12 allelic variants described herein are dwf12-1 through dwf12-2. These variants are discussed in detail below.

The term "dwf12 phenotype" as used herein refers to any microscopic or macroscopic change in structure or morphology of a plant, such as a transgenic plant, as well as biochemical differences, which are characteristic of a dwf12 mutant plant, as compared to a progenitor, wild-type plant cultivated under the same conditions. Biochemical differences include reduced or increased SHAGGY kinase activity as compared to the wild-type polypeptide, as well as substrate recognition and/or the ability to act as a substrate for another molecule. Reduced activity, for example, may in turn result an accumulation of significant amounts of BRs, such as brassinolide. Generally, morphological differences include a short robust stature, short internodes, an increased number of inflorescences, and small dark-green, round leaves similar to the phenotype previously reported for the other BR dwarfs (Azpiroz, et al., 1998; Choe, et al., 1999a, 1999b). The height of such plants will typically be 75% or less of the wild-type plant, more typically 50% or less of the wild-type plant, and even more typically 25% or less of the wild-type plant, or any integer in between. Moreover, particularly unique to dwf12 plants, is the presence of severe downward curling of leaves. The morphological and biochemical differences described herein may arise from inhibition of transcription or translation, or from protein activity.

Thus, by dwf12 phenotype is meant an increase or decrease in any of the following activities which are associated with the presence or absence of a dwf12 polynucleotide or polypeptide sequence: SHAGGY kinase activity, as measured by standard activity assays (see, e.g., Bianchi et al., *Mol. Gen. Genet.* (1994) 242:337-345); brassinosteroid biosynthesis; sterol composition; cell cycle; cell elongation and division; seed number; seed size; seed viability; organ size such as silique length, internodes, leaves, stems, pedicels and petioles; increased number of inflorescences; and severe downward curling of leaves.

A "polypeptide" is used in it broadest sense to refer to a compound of two or more subunit amino acids, amino acid analogs, or other peptidomimetics. The subunits may be linked by peptide bonds or by other bonds, for example ester, ether, etc. As used herein, the term "amino acid" refers to either natural and/or unnatural or synthetic amino acids, including glycine and both the D or L optical isomers, and amino acid analogs and peptidomimetics. A peptide of three or more amino acids is commonly called an oligopeptide if the peptide chain is short. If the peptide chain is long, the peptide is typically called a polypeptide or a protein. Full-length proteins, analogs, and fragments thereof are encompassed by the definition. The terms also include postexpression modifications of the polypeptide, for example, glycosylation, acetylation, phosphorylation and the like. Furthermore, as ionizable amino and carboxyl groups are present in the molecule, a particular polypeptide may be obtained as an acidic or basic salt, or in neutral form. A polypeptide may be obtained directly from the source organism, or may be recombinantly or synthetically produced (see further below).

A "DWF12" polypeptide is a polypeptide as defined above, which functions in a brassinolide (BL) signaling pathway featuring the receptor kinase BRI1. As explained herein, DWF12 is a member of the SHAGGY kinase family of proteins. The native sequence of full-length DWF12 is shown in FIG. 3. However, the term encompasses mutants and fragments of the native sequence so long as the protein functions for its intended purpose, i.e., to produce a dwf12 mutant phenotype as defined herein.

The term "dwf12 mutant" or "dwf12 analog" refers to derivatives of DWF12, or fragments of such derivatives, that retain desired function, e.g., impart at least one dwf12 phenotype, as described herein. In general, the term refers to compounds having a native polypeptide sequence and structure with one or more amino acid additions, substitutions and/or deletions, relative to the native molecule, so long as the modifications impart the desired phenotype. The dwf12 mutants may be made from dwf12 mutant polynucleotide sequences. Methods for making mutants are known in the art and are described further below. Preferred mutants are also described below.

Mutants may include either non-conservative or conservative amino acid substitutions. Conservative substitutions are those substitutions that take place within a family of amino acids that are related in their side chains. Specifically, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids. For example, it is reasonably predictable that an isolated replacement of leucine with isoleucine or valine, an aspartate with a glutamate, a threonine with a serine, or a similar conservative replacement of an amino acid with a structurally related amino acid, will not have a major effect on the biological activity. It is to be understood that the terms include the various sequence polymorphisms that exist, wherein amino acid substitutions in the protein sequence do not affect the essential functions of the protein.

In the context of the present invention, non-conservative amino acid substitutions in conserved domains are preferred. Such conserved domains are specified above and include the casein kinase II phosphorylation domains, the protein kinase C phosphorylation domains, the active site lysine residue, the tyrosine phosphorylation domain, the protein kinase ATP-binding domain, the eukaryotic protein kinase ATP-binding domain, the eukaryotic protein kinase substrate-binding domain, the eukaryotic protein kinase signature sequence, the glycosylation domains, as well as a non-conservative substitution within the conserved sequences CDFGSAK and SYICSR. The positions of these various domains relative to DWF12 are denoted above and in FIG. 3. One of skill in the art can readily identify the corresponding domains in DWF12 homologues.

By "purified" and "isolated" is meant, when referring to a polypeptide or polynucleotide, that the molecule is separate and discrete from the whole organism with which the molecule is found in nature; or devoid, in whole or part, of sequences normally associated with it in nature; or a sequence, as it exists in nature, but having heterologous sequences (as defined below) in association therewith. It is to be understood that the term "isolated" with reference to a polynucleotide intends that the polynucleotide is separate and discrete from the chromosome from which the polynucleotide may derive. The term "purified" as used herein preferably means at least 75% by weight, more preferably at least 85% by weight, more preferably still at least 95% by weight, and most preferably at least 98% by weight, of biological macromolecules of the same type are present. An "isolated polynucleotide which encodes a particular polypeptide" refers to a nucleic acid molecule which is substantially free of other nucleic acid molecules that do not encode the subject polypeptide; however, the molecule may include some additional bases or moieties which do not deleteriously affect the basic characteristics of the composition.

By "fragment" is intended a polypeptide or polynucleotide consisting of only a part of the intact sequence and structure of the reference polypeptide or polynucleotide, respectively. The fragment can include a 3' or C-terminal deletion or a 5' or N-terminal deletion, or even an internal deletion, of the native molecule. A polynucleotide fragment of a particular sequence will generally include at least about 15 contiguous bases of the molecule in question, more preferably 18-25 contiguous bases, even more preferably 30-50 or more contiguous bases of the molecule, or any integer between 15 bases and the full-length sequence of the molecule. Fragments which provide at least one dwf12 phenotype as defined above are useful in the production of transgenic plants. Fragments are also useful as oligonucleotide probes, to find additional related sequences.

Similarly, a polypeptide fragment of a protein molecule will generally include at least about 10 contiguous amino acid residues of the full-length molecule, preferably at least about 15-25 contiguous amino acid residues of the full-length molecule, and most preferably at least about 20-50 or more contiguous amino acid residues of the full-length DWF12 molecule, or any integer between 10 amino acids and the full-length sequence of the molecule. Such fragments are useful for the production of antibodies and the like.

By "transgenic plant" is meant a plant into which one or more exogenous polynucleotides has been introduced. Examples of means by which this can be accomplished are described below, and include Agrobacterium-mediated transformation, biolistic methods, electroporation, and the like. In the context of the present invention, the transgenic plant contains a polynucleotide which is not normally present in the corresponding wild-type plant and which confers at least one altered trait, such as an altered dwf12 phenotypic trait, to the plant. The transgenic plant therefore exhibits altered structure, morphology or biochemistry as compared with a progenitor plant which does not contain the transgene, when the transgenic plant and the progenitor plant are cultivated under similar or equivalent growth conditions. Such a plant containing the exogenous polynucleotide is referred to here as an $R_1$ generation transgenic plant. Transgenic plants may also arise from sexual cross or by selfing of transgenic plants into which exogenous polynucleotides have been introduced. Such a plant containing the exogenous nucleic acid is also referred to here as an $R_1$ generation transgenic plant. Transgenic plants which arise from a sexual cross with another parent line or by selfing are "descendants or the progeny" of a $R_1$ plant and are generally called $F_n$ plants or $S_n$ plants, respectively, n meaning the number of generations.

II. Modes of Carrying Out the Invention

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

Brief Description

The present invention relates to molecules involved in the brassinosteroid (BR) signaling pathways and mutants thereof. Compared to the flurry of BR biosynthetic mutants, a dearth of mutants defective in the BR signaling pathway has made it difficult to obtain additional components of BR signaling. To find other players in the pathway featuring the receptor kinase BRI1, the inventors herein performed extensive screening of EMS-mutant populations and have isolated novel BR-insensitive mutants in dwarf12. dwf12 mutants share many characteristic phenotypes of previously reported BR mutants, such as short stature, short round leaves, reduced fertility, reduced fecundity, and abnormal de-etiolation. dwf12 mutants also have a unique phenotype, severe downward curling of leaves. Interestingly, plants heterozygous for these mutations show a dwarf phenotype whose height is intermediate between wild-type and homozygous mutant plants, suggesting that the dwf12 mutations are dominant-negative, gain of function, or haploinsufficent. Further morphometric analysis of two dwf12 alleles, dwf12-1 (also termed dwf12-1D) and dwf12-2 (also termed dwf12-2D), indicates that the dwf12-2 mutation results in more severe phenotypes than those of dwf12-1. Similar to bri1/dwf2, dwf12 plants accumulate a significant amount of BRs including brassinolide. The inventors identified DWF12 using map-based cloning. DWF12 encodes a conserved protein predicted to reside in the cytoplasm. Without being bound by a particular theory, DWF12 appears to act downstream of BRI in a phosphorylation cascade, ultimately leading to the activation of BR-dependent transcriptional events.

In particular, DWF12 is believed to be a member of the SHAGGY kinase family of proteins. The SHAGGY kinases are serine/threonine protein kinases. This family of proteins is characterized by a highly conserved catalytic protein kinase domain. These proteins display about 70% sequence identity to SHAGGY (SGG) and glycogen synthase kinase-3 (GSK-3) from *Drosophila* and rat, respectively. However, the proteins vary at their amino and carboxyl termini. Table 1 shows GenBank accession numbers for various sequences derived from plants with significant homology to DWF12.

TABLE 1

| GenBank Accession No. | Plant Species |
|---|---|
| 1161511 | *Arabadopsis thaliana* |
| 1161509 | *A. thaliana* |
| 1480077 | *A. thaliana* |
| 2444276 | *A. thaliana* |
| 2182028 | *Oryza sativa* |
| 456508 | *A. thaliana* |
| 619893 | *Petunia hybrida* |
| 13620844 | *O. sativa* |
| 456355 | *Nicotiana tabacum* |
| 460831 | *A. thaliana* |
| 1769888 | *A. thaliana* |
| 313143 | *Medicago sativa* |
| 313147 | *M. sativa* |
| 313145 | *M. sativa* |
| 1944517 | *A. thaliana* |
| 1617199 | *N. tabacum* |
| 3236114 | *N. tabacum* |
| 2569949 | *B. napus* |
| 2598602 | *N. tabacum* |
| 2911532 | *P. hybrida* |
| 2598600 | *N. tabacum* |
| 1431621 | *T. repens* |
| 10185113 | *M. sativa* |
| 1504062 | *A. thaliana* |
| 1627515 | *A. thaliana* |
| 2569930 | *A. thaliana* |
| 18773961 | *Ricinus communis* |
| 3928147 | *Cicer arietinum* |

One representative DWF12 sequence is shown in FIG. 3. Amino acids 38-326 of FIG. 3 represent the protein kinase domain that shows homology to other SHAGGY kinase family members. Thus, amino acids 1-37 and 327-380 represent the N- and C-terminal variable regions, respectively. Without being bound by a particular theory, a region within amino acids 1-37 may be important for the BR signaling cascade. Thus, this region, either alone or in combination with other heterologous sequences, may be useful for modulating the BR signaling cascade in a wide variety of plants. Also indicated in the figure are the casein kinase II phosphorylation domains (designated as "CK2_PHOSPHO_SITE"); the protein kinase C phosphorylation domains (designated as "PKC_PHOSPHO_SITE"); the tyrosine phosphorylation domain (designated as "TYR_PHOSPHO_SITE"); the phosphokinase domain signature (designated "PK Domain signature); and the asparagine glycosylation sites. Additionally, the Tyr shown at position 200 is highly conserved and believed to be important for activity. Other highly conserved motifs include the sequence CDFGSAK, found at positions 183-189 of FIG. 3, as well as the sequence SYICSR, found at positions 199-204 of FIG. 3.

Of particular interest, is the production of mutants of the wild-type sequence, which mutants, when used to produce transgenic plants, result in altered phenotypes relative to the wild-type plant. Particularly preferred mutants are those which have one or more mutations in the conserved sequences described above and shown in FIG. 3. Particularly preferred are mutants with one or more non-conservative amino acid substitutions in one or more of the conserved domains.

Representative mutants include, but are not limited to, dwf12 mutant polypeptides with at least about 70% sequence identity to the polypeptide depicted at positions 38-326 or 1-380 of FIG. 3. The polypeptide comprises a mutation comprising at least one non-conservative substitution, deletion or addition to an amino acid in a region of the polypeptide depicted in FIG. 3, wherein the region is one or more of (a) a casein kinase II phosphorylation domain spanning positions 104-106 of FIG. 3; (b) a casein kinase II phosphorylation domain spanning positions 220-223 of FIG. 3; (c) a casein kinase II phosphorylation domain spanning positions 261-264 of FIG. 3; (d) a casein kinase II phosphorylation domain spanning positions 314-317 of FIG. 3; (e) a casein kinase II phosphorylation domain spanning positions 353-356 (f) a protein kinase C phosphorylation domain spanning positions 104-106 of FIG. 3; (g) a protein kinase C phosphorylation domain spanning positions 187-189 of FIG. 3; (h) a protein kinase C phosphorylation domain spanning positions 310-312; (i) the active site lysine residue found at position 69 of FIG. 3; (j) a tyrosine phosphorylation domain spanning positions 70-77 of FIG. 3; (k) a protein kinase ATP-binding domain spanning positions 46-69 of FIG. 3; (l) a eukaryotic protein kinase ATP-binding domain spanning positions 157-172 of FIG. 3; (m) a eukaryotic protein kinase substrate-binding domain spanning positions 218-228 of FIG. 3; (n) a eukaryotic protein kinase signature sequence spanning positions 316-327 of FIG. 3; (o) a glycosylation domain spanning positions 197-200 of FIG. 3; or (p) a glycosylation domain spanning positions 376-379 of FIG. 3. Additionally, the mutation may occur within other conserved sequences, such as the sequence CDFGSAK, found at positions 183-189 of FIG. 3, as well as the sequence SYICSR, found at positions 199-204 of FIG. 3.

Alternatively, the isolated dwf12 mutant polypeptide has at least about 70% sequence identity to a polypeptide designated in Table 1, and has one or more mutations above, in a domain corresponding to the domains set forth above. For example, the consensus sequences for the various domains are known. Thus, one of skill in the art can readily identify these regions in other related polypeptides and make appropriate mutations to alter the function of the polypeptide. For example, the consensus sequence for tyrosine kinase phosphorylation sites is known to be [RK]-x(2,3)-[DE]-x(2,3)-Y, where brackets in the formula denote one or the other of amino acids, i.e., R or K, followed by 2 or 3 variable amino acids, then D or E followed by 2 or 3 variable amino acids sequences, followed by Y. The consensus sequence for a protein kinase C phosphorylation site is [ST]-x-[RK]. The consensus sequence for a casein kinase II phosphorylation site is [ST]-x(2)-[DE]. The consensus sequence for an N-glycosylation site is N—{P}—[ST]-{P}.

In certain embodiments, the mutation comprises a change in a casein kinase II phosphorylation domain as specified above and in FIG. 3, of an acidic amino acid residue such as Asp or Glu, to a basic amino acid residue, such as Lys, Arg or His. In other embodiments, the mutation comprises a change in a protein kinase C phosphorylation domain as specified above of a basic amino acid residue to an acidic amino acid residue.

Additionally, the mutation may comprise a mutation to the sequence spanning positions 261-264 of FIG. 3, such as a change of Glu-263, or Glu-264, to Lys. These particular mutations are characteristic of the dwf12-1 and dwf12-2 mutants described herein.

The molecules of the present invention are useful in the production of transgenic plants which display at least one altered phenotype, such as a dwf12 phenotype, so that the resulting plants have altered biochemistry, structure or morphology. The present invention particularly provides for plants with increased or decreased SHAGGY kinase activity. This, in turn, may result in altered structure or morphology such as downward curling of leaves, increased or reduced cell length, extended or reduced flowering periods, increased or reduced size of leaves or fruit, increased or reduced branching, increased or reduced seed production and altered sterol composition relative to wild-type plants. Thus, the invention provides for modulating any of these traits, including biomass; height; tissue or organ size, such as but not limited to leaf, seed, root, flower, stem, petioles, internodes, hypocotyl size; fertility; fecundity; mechanical sterility, e.g., due to the failure of filaments to elongate; leaf curling, including the rosette and/or cauline; cell elongation; and stress tolerance, such as the ability to tolerate changes in temperature, including the ability to tolerate cold conditions, heat, drought, salt and herbicides, especially during critical times of growth. Such stress tolerance is particularly useful for the production of commercially useful transgenic crops, described in detail below.

In certain embodiments, the trait is modulated by modulating expression of an endogenous SHAGGY kinase by inserting a polynucleotide into a cell wherein said polynucleotide encodes for a SHAGGY kinase exhibiting reduced activity as compared to the corresponding endogenous SHAGGY kinase, such as a polynucleotide that encodes a mutant dwf12 polypeptide with reduced activity. The polynucleotide may be heterologous to the cell, i.e., it may be derived from a different plant species than the cell, and/or the polynucleotide may comprise multiple copies of the mutant SHAGGY kinase. The SHAGGY kinase modulated is preferably one involved in a BR signaling pathway, such as DWF12 or a homologue thereof. The polynucleotide may also encode a SHAGGY kinase exhibiting at least the same or enhanced activity as compared to the corresponding endogenous SHAGGY kinase, such as a polynucleotide that encodes a mutant dwf12 polypeptide with enhanced activity or a homologue thereof. Moreover, the polynucleotide may be one that is capable of hybridizing to the endogenous SHAGGY kinase mRNA.

Thus, the dwf12 mutant polypeptides described herein can be expressed to engineer a plant with desirable properties. The engineering is accomplished by transforming plants with nucleic acid constructs described herein which may also comprise promoters and secretion signal peptides. The transformed plants or their progenies are screened for plants that express the desired polypeptide.

Engineered plants exhibiting the desired altered structure or morphology can be used in plant breeding or directly in agricultural production or industrial applications. Plants having the altered polypeptide can be crossed with other altered plants engineered with alterations in other growth modulation enzymes, proteins or polypeptides to produce lines with even further enhanced altered structural morphology characteristics compared to the parents or progenitor plants.

Isolation of Nucleic Acid Sequences From Plants

The isolation of DWF12 and mutant dwf12 sequences may be accomplished by a number of techniques. For instance, oligonucleotide probes based on the sequences disclosed herein can be used to identify the desired gene in a cDNA or genomic DNA library from a desired plant species. To construct genomic libraries, large segments of genomic DNA are generated by random fragmentation, e.g. using restriction endonucleases, and are ligated with vector DNA to form concatemers that can be packaged into the appropriate vector. To prepare a library of tissue-specific cDNAs, mRNA is isolated from tissues and a cDNA library which contains the gene transcripts is prepared from the mRNA.

The cDNA or genomic library can then be screened using a probe based upon the sequence of a cloned gene such as the polynucleotides disclosed herein. Probes may be used to hybridize with genomic DNA or cDNA sequences to isolate homologous genes in the same or different plant species. Alternatively, the nucleic acids of interest can be amplified from nucleic acid samples using amplification techniques. For instance, polymerase chain reaction (PCR) technology to amplify the sequences of the genes directly from mRNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes.

Appropriate primers and probes for identifying DWF12-specific genes from plant tissues are generated from comparisons of the sequences provided herein. For a general overview of PCR see Innis et al. eds, *PCR Protocols: A Guide to Methods and Applications*, Academic Press, San Diego (1990). Appropriate primers for this invention include, for instance, those primers described in the Examples, as well as other primers derived from the DWF12 and mutant dwf12 sequences disclosed herein. Suitable amplification conditions may be readily determined by one of skill in the art in view of the teachings herein, for example, including reaction components and amplification conditions as follows: 10 mM Tris-HCl, pH 8.3, 50 mM potassium chloride, 1.5 mM magnesium chloride, 0.001% gelatin, 200 μM dATP, 200 μM dCTP, 200 μM dGTP, 200 μM dTTP, 0.4 μM primers, and 100 units per mL Taq polymerase; 96° C. for 3 min., 30 cycles of 96° C. for 45 seconds, 50° C. for 60 seconds, 72° C. for 60 seconds, followed by 72° C. for 5 min.

Polynucleotides may also be synthesized by well-known techniques as described in the technical literature. See, e.g., Carruthers, et al. (1982) *Cold Spring Harbor Symp. Quant. Biol.* 47:411418, and Adams, et al. (1983) *J. Am. Chem. Soc.* 105:661. Double stranded DNA fragments may then be obtained either by synthesizing the complementary strand and annealing the strands together under appropriate conditions, or by adding the complementary strand using DNA polymerase with an appropriate primer sequence.

The polynucleotides of the present invention may also be used to isolate or create other mutant cell gene alleles. Mutagenesis consists primarily of site-directed mutagenesis followed by phenotypic testing of the altered gene product. Some of the more commonly employed site-directed mutagenesis protocols take advantage of vectors that can provide single stranded as well as double stranded DNA, as needed. Generally, the mutagenesis protocol with such vectors is as follows. A mutagenic primer, i.e., a primer complementary to the sequence to be changed, but consisting of one or a small number of altered, added, or deleted bases, is synthesized. The primer is extended in vitro by a DNA polymerase and, after some additional manipulations, the now double-stranded DNA is transfected into bacterial cells. Next, by a variety of methods, the desired mutated DNA is identified, and the desired protein is purified from clones containing the mutated sequence. For longer sequences, additional cloning steps are often required because long inserts (longer than 2 kilobases) are unstable in those vectors. Protocols are known to one skilled in the art and kits for site-directed mutagenesis are widely available from biotechnology supply companies, for example from Amersham Life Science, Inc. (Arlington Heights, Ill.) and Stratagene Cloning Systems (La Jolla, Calif.).

Control Elements

Regulatory regions can be isolated from the DWF12 gene and used in recombinant constructs for modulating the expression of the DWF12 gene or of a heterologous gene in vitro and/or in vivo. As shown in FIG. 1, the coding region of the DWF12 gene begins at nucleotide position 200. The region of the gene spanning nucleotide positions 1-199 of FIG. 1 includes a DWF12 5' UTR. This region may be used in its entirety or fragments of the region may be isolated which may provide regulatory functions related to, for example, translation rate and mRNA stability.

The DWF12 promoter is situated approximately 2 kb upstream from the 5' UTR and can be readily identified by analyzing the 5' sequences of a genomic clone corresponding to the DWF12-specific genes described herein. Sequences characteristic of promoter sequences can be used to identify the promoter. Sequences controlling eukaryotic gene expression have been extensively studied. For instance, promoter sequence elements include the TATA box consensus sequence (TATAAT), which is usually 20 to 30 base pairs upstream of the transcription start site. In most instances the TATA box is required for accurate transcription initiation. In plants, further upstream from the TATA box, at positions −80 to −100, there is typically a promoter element with a series of adenines surrounding the trinucleotide G (or T) N G. (See, J. Messing et al., in *Genetic Engineering in Plants*, pp. 221-227 (Kosage, Meredith and Hollaender, eds. (1983)). Methods for identifying and characterizing promoter regions in plant genomic DNA are described, for example, in Jordano et al. (1989) *Plant Cell* 1:855-866; Bustos et al (1989) *Plant Cell* 1:839-854; Green et al. (1988) *EMBO J.* 7:40354044; Meier et al. (1991) *Plant Cell* 3:309-316; and Zhang et al (1996) *Plant Physiology* 110: 1069-1079).

Additionally, the promoter region may include nucleotide substitutions, insertions or deletions that do not substantially affect the binding of relevant DNA binding proteins and hence the promoter function. It may, at times, be desirable to decrease the binding of relevant DNA binding proteins to "silence" or "down-regulate" a promoter, or conversely to increase the binding of relevant DNA binding proteins to "enhance" or "up-regulate" a promoter. In such instances, the nucleotide sequence of the promoter region may be modified by, e.g., inserting additional nucleotides, changing the identity of relevant nucleotides, including use of chemically-modified bases, or by deleting one or more nucleotides.

Promoter function can be assayed by methods known in the art, preferably by measuring activity of a reporter gene operatively linked to the sequence being tested for promoter function. Examples of reporter genes include those encoding luciferase, green fluorescent protein, GUS, neo, cat and bar.

Polynucleotides comprising untranslated (UTR) sequences and intron/exon junctions are also within the scope of the invention. UTR sequences include introns and 5' or 3' untranslated regions (5' UTRs or 3' UTRs). Introns and exons are shown in FIG. 1. Specifically, introns are those sequences which do not have amino acid sequences shown below the nucleotide sequence. These portions of the DWF12 gene especially UTRs, can have regulatory functions related to, for example, translation rate and mRNA stability. Thus, these portions of the gene can be isolated for use as elements of gene constructs for expression of polynucleotides encoding desired polypeptides.

Introns of genomic DNA segments may also have regulatory functions. Sometimes promoter elements, especially transcription enhancer or suppressor elements, are found within introns. Also, elements related to stability of heteronuclear RNA and efficiency of transport to the cytoplasm for translation can be found in intron elements. Thus, these segments can also find use as elements of expression vectors intended for use to transform plants.

The introns, UTR sequences and intron/exon junctions can vary from the native sequence. Such changes from those sequences preferably will not affect the regulatory activity of the UTRs or intron or intron/exon junction sequences on expression, transcription, or translation. However, in some instances, down-regulation of such activity may be desired to modulate traits or phenotypic or in vitro activity.

Use of Nucleic Acids of the Invention to Inhibit Gene Expression

The isolated sequences prepared as described herein, can be used to prepare expression cassettes useful in a number of techniques. For example, expression cassettes of the invention can be used to suppress (underexpress) endogenous DWF12 gene expression, as well as expression of other SHAGGY kinases, especially those involved in BR signaling pathways. Inhibiting expression can be useful, for instance, in producing or suppressing phenotypes as described above (e.g., dwarf appearance) exhibited by dwf12 plants. Further, the inhibitory polynucleotides of the present invention can also be used in combination with overexpressing constructs described below, for example, using suitable tissue-specific promoters linked to polynucleotides described herein. In this way, the polynucleotides can be used to promote dwf12 phenotypes (e.g., activity) in selected tissue and, at the same time, inhibit dwf12 phenotypes (e.g., activity) in different tissue(s).

A number of methods can be used to inhibit gene expression in plants. For instance, antisense technology can be conveniently used. To accomplish this, a nucleic acid segment from the desired gene is cloned and operably linked to a promoter such that the antisense strand of RNA will be transcribed. The expression cassette is then transformed into plants and the antisense strand of RNA is produced. In plant cells, it has been suggested that antisense RNA inhibits gene expression by preventing the accumulation of mRNA which encodes the enzyme of interest, see, e.g., Sheehy et al (1988) *Proc. Nat. Acad. Sci. USA* 85:8805-8809, and Hiatt et al., U.S. Pat. No. 4,801,340.

The nucleic acid segment to be introduced generally will be substantially identical to at least a portion of the endogenous gene or genes to be repressed. The sequence, however, need not be perfectly identical to inhibit expression. The vectors of the present invention can be designed such that the inhibitory effect applies to other proteins within a family of genes exhibiting homology or substantial homology to the target gene.

For antisense suppression, the introduced sequence also need not be full length relative to either the primary transcription product or fully processed mRNA. Generally, higher homology can be used to compensate for the use of a shorter sequence. Furthermore, the introduced sequence need not have the same intron or exon pattern, and homology of non-coding segments may be equally effective. Normally, a sequence of between about 30 or 40 nucleotides and about full length nucleotides should be used, though a sequence of at least about 100 nucleotides is preferred, a sequence of at least about 200 nucleotides is more preferred, and a sequence of at least about 500 nucleotides is especially preferred. It is to be understood that any integer between the above-recited ranges is intended to be captured herein.

Catalytic RNA molecules or ribozymes can also be used to inhibit expression of DWF12 or other SHAGGY kinase genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs.

A number of classes of ribozymes have been identified. One class of ribozymes is derived from a number of small circular RNAs which are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, lucerne transient streak virus, velvet tobacco mottle virus, solanum nodiflorum mottle virus and subterranean clover mottle virus. The design and use of target RNA-specific ribozymes is described in Haseloff et al (1988) *Nature* 334:585-591.

Another method of suppression is sense suppression. Introduction of expression cassettes in which a nucleic acid is configured in the sense orientation with respect to the promoter has been shown to be an effective means by which to block the transcription of target genes. For an example of the use of this method to modulate expression of endogenous genes see, Napoli et al (1990) *The Plant Cell* 2:279-289 and U.S. Pat. Nos. 5,034,323, 5,231,020, and 5,283,184.

Generally, where inhibition of expression is desired, some transcription of the introduced sequence occurs. The effect may occur where the introduced sequence contains no coding sequence per se, but only intron or untranslated sequences homologous to sequences present in the primary transcript of the endogenous sequence. The introduced sequence generally will be substantially identical to the endogenous sequence intended to be repressed. This minimal identity will typically be greater than about 50%-65%, but a higher identity might exert a more effective repression of expression of the endogenous sequences. Substantially greater identity of more than about 80% is preferred, though about 95% to absolute identity would be most preferred. It is to be understood that any integer between the above-recited ranges is intended to be captured herein. As with antisense regulation, the effect should apply to any other proteins within a similar family of genes exhibiting homology or substantial homology.

For sense suppression, the introduced sequence in the expression cassette, needing less than absolute identity, also need not be full length, relative to either the primary transcription product or fully processed mRNA. This may be preferred to avoid concurrent production of some plants which are overexpressers. A higher identity in a shorter than full length sequence compensates for a longer, less identical sequence. Furthermore, the introduced sequence need not have the same intron or exon pattern, and identity of non-coding segments will be equally effective. Normally, a sequence of the size ranges noted above for antisense regulation is used.

Use of Nucleic Acids of the Invention to Enhance Gene Expression

In addition to inhibiting certain features of a plant, the polynucleotides of the invention can be used to increase certain features such as extending flowering, producing larger leaves or fruit, producing increased branching and increasing seed production. This can be accomplished by the overexpression of DWF12 polynucleotides.

The exogenous DWF12 polynucleotides and dwf12 mutant polynucleotides do not have to code for exact copies of the endogenous DWF12 proteins. Modified DWF12 protein chains can also be readily designed utilizing various recombinant DNA techniques well known to those skilled in the art and described for instance, in Sambrook et al., supra. Hydroxylamine can also be used to introduce single base mutations into the coding region of the gene (Sikorski et al (1991) *Meth. Enzymol.* 194: 302-318). For example, the chains can vary from the naturally occurring sequence at the primary structure level by amino acid substitutions, additions, deletions, and the like. These modifications can be used in a number of combinations to produce the final modified protein chain.

It will be apparent that the polynucleotides described herein can be used in a variety of combinations. For example, the polynucleotides can be used to produce different phenotypes in the same organism, for instance by using tissue-specific promoters to overexpress a DWF12 or mutant dwf12 polynucleotide in certain tissues (e.g., leaf tissue and other promoters described herein) while at the same time using tissue-specific promoters to inhibit expression of DWF12 or mutant dwf12 in other tissues. In addition, fusion proteins of the polynucleotides described herein with other known polynucleotides (e.g., polynucleotides encoding products involved in the BR pathway) can be constructed and employed to obtain desired phenotypes.

Any of the DWF12 polynucleotides and mutant dwf12 polynucleotides described herein can also be used in standard diagnostic assays, for example, in assays mRNA levels (see, Sambrook et al, supra); as hybridization probes, e.g., in combination with appropriate means, such as a label, for detecting hybridization (see, Sambrook et al., supra); as primers, e.g., for PCR (see, Sambrook et al., supra); attached to solid phase supports and the like.

Preparation of Recombinant Vectors

To use isolated sequences in the above techniques, recombinant DNA vectors suitable for transformation of plant cells are prepared. Techniques for transforming a wide variety of higher plant species are well known and described further below as well as in the technical and scientific literature. See, for example, Weising et al (1988) *Ann. Rev. Genet.* 22:421-477. A DNA sequence coding for the desired polypeptide, for example a cDNA sequence encoding the full length DWF12 protein or mutant protein, will preferably be combined with transcriptional and translational initiation regulatory sequences which will direct the transcription of the sequence from the gene in the intended tissues of the transgenic plant.

Such regulatory elements include but are not limited to the promoters derived from the genome of plant cells (e.g., heat shock promoters such as soybean hsp17.5-E or hsp17.3-B (Gurley et al. (1986) *Mol. Cell. Biol.* 6:559-565); the promoter for the small subunit of RUBISCO (Coruzzi et al. (1984) *EMBO J.* 3:1671-1680; Broglie et al (1984) *Science* 224:838-843); the promoter for the chlorophyll a/b binding protein) or from plant viruses viral promoters such as the 35S RNA and 19S RNA promoters of CaMV (Brisson et al. (1984) *Nature* 310:511-514), or the coat protein promoter of TMV (Takamatsu et al. (1987) *EMBO J.* 6:307-311), cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3-phosphoglycerate kinase, the promoters of acid phosphatase, heat shock promoters (e.g., as described above) and the promoters of the yeast alpha-mating factors.

In construction of recombinant expression cassettes of the invention, a plant promoter fragment may be employed which will direct expression of the gene in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the T-DNA mannopine synthetase promoter (e.g., the 1'- or 2'-promoter derived from T-DNA of *Agrobacterium tumafaciens*), and other transcription initiation regions from various plant genes known to those of skill.

Alternatively, the plant promoter may direct expression of the polynucleotide of the invention in a specific tissue (tissue-specific promoters) or may be otherwise under more precise environmental control (inducible promoters). Examples of tissue-specific promoters under developmental control include promoters that initiate transcription only in certain tissues, such as fruit, seeds, or flowers such as tissue- or developmental-specific promoter, such as, but not limited to the cell promoter, the CHS promoter, the PATATIN promoter, etc. The tissue specific E8 promoter from tomato is particularly useful for directing gene expression so that a desired gene product is located in fruits.

Other suitable promoters include those from genes encoding embryonic storage proteins. Examples of environmental conditions that may affect transcription by inducible promoters include anaerobic conditions, elevated temperature, or the presence of light. Moreover, promoters inducible by particular chemicals, such as herbicides and insecticides, may be used to express the polynucleotide of interest.

If proper polypeptide expression is desired, a polyadenylation region at the 3'-end of the coding region should be included. The polyadenylation region can be derived from the natural gene, from a variety of other plant genes, or from T-DNA. In addition, the promoter itself can be derived from the DWF12 genomic sequence, as described above.

The particular promoter for use in the constructs of the present invention is largely a matter of choice and will depend on the desired outcome and on the particular SHAGGY kinase gene, such as DWF12 or dwf12 mutant gene to be used. For example, if reduced overall structure is desired, promoters specific for elongating cells in the shoot apical meristem can be recombined with semi-dominant dwarf alleles, such as dwf12-1 or dwf12-2. If reduced organ size is desired, promoters specific for leaves, flowers, stems and roots can be recombined with semi-dominant dwarf alleles. If stress tolerance to, e.g., cold, drought, heat, salt, etc. is desired, inducible promoters can be recombined with a wild-type copy of the DWF12 gene. In order to produce larger plants or organs, organ-specific promoters (organ size increase) or ectopic-overexpression and meristem-specific promoters (whole plant size increase) may be recombined with a wild-type copy of the DWF12 gene. For increased seed yield, ectopic-overexpression or floral meristem-specific promoters may be recombined with a wild-type copy of the DWF12 gene.

The vector comprising the sequences (e.g., promoters or coding regions) from genes of the invention will typically comprise a marker gene which confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosluforon or Basta.

Production of Transgenic Plants

DNA constructs of the invention may be introduced into the genome of the desired plant host by a variety of conventional techniques. For reviews of such techniques see, for example, Weissbach & Weissbach *Methods for Plant Molecular Biology* (1988, Academic Press, N.Y.) Section VIII, pp. 421-463; and Grierson & Corey, *Plant Molecular Biology* (1988, 2d Ed.), Blackie, London, Ch. 7-9. For example, the DNA construct may be introduced directly into the genomic DNA of the plant cell using techniques such as electroporation and microinjection of plant cell protoplasts, or the DNA constructs can be introduced directly to plant tissue using biolistic methods, such as DNA particle bombardment (see, e.g., Klein et al (1987) *Nature* 327:70-73). Alternatively, the DNA constructs may be combined with suitable T-DNA flanking regions and introduced into a conventional *Agrobacterium tumefaciens* host vector. *Agrobacterium tumefaciens*-mediated transformation techniques, including disarming and use of binary vectors, are well described in the scientific literature. See, for example Horsch et al (1984) *Science* 233:496-498, and Fraley et al (1983) *Proc. Nat'l. Acad. Sci. USA* 80:4803. The virulence functions of the *Agrobacterium tumefaciens* host will direct the insertion of the construct and adjacent marker into the plant cell DNA when the cell is infected by the bacteria using binary T DNA vector (Bevan (1984) *Nuc. Acid Res.* 12:8711-8721) or the co-cultivation procedure (Horsch et al (1985) *Science* 227:1229-1231). Generally, the *Agrobacterium* transformation system is used to engineer dicotyledonous plants (Bevan et al (1982) *Ann. Rev. Genet* 16:357-384; Rogers et al (1986) *Methods Enzymol.* 118:627-641). The *Agrobacterium* transformation system may also be used to transform, as well as transfer, DNA to monocotyledonous plants and plant cells. (see Hernalsteen et al (1984) *EMBO J* 3:3039-3041; Hooykass-Van Slogteren et al (1984) *Nature* 311:763-764; Grimsley et al (1987) *Nature* 325:1677-179; Boulton et al (1989) *Plant Mol. Biol.* 12:3140; and Gould et al (1991) *Plant Physiol.* 95:426-434).

Alternative gene transfer and transformation methods include, but are not limited to, protoplast transformation through calcium-, polyethylene glycol (PEG)- or electroporation-mediated uptake of naked DNA (see Paszkowski et al. (1984) *EMBO J* 3:2717-2722, Potrykus et al. (1985) *Molec. Gen. Genet.* 199:169-177; Fromm et al. (1985) *Proc. Nat. Acad. Sci. USA* 82:5824-5828; and Shimamoto (1989) *Nature* 338:274-276) and electroporation of plant tissues (D'Halluin et al. (1992) *Plant Cell* 4:1495-1505). Additional methods for plant cell transformation include microinjection, silicon carbide mediated DNA uptake (Kaeppler et al. (1990) *Plant Cell Reporter* 9:415-418), and microprojectile bombardment (see Klein et al. (1988) *Proc. Nat. Acad. Sci. USA* 85:4305-4309; and Gordon-Kamm et al. (1990) *Plant Cell* 2:603-618).

Transformed plant cells which are produced by any of the above transformation techniques can be cultured to regenerate a whole plant which possesses the transformed genotype and thus the desired phenotype. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans, et al., "Protoplasts Isolation and Culture" in *Handbook of Plant Cell Culture*, pp. 124-176, Macmillian Publishing Company, New York, 1983; and Binding, *Regeneration of Plants, Plant Protoplasts*, pp. 21-73, CRC Press, Boca Raton, 1985. Regeneration can also be obtained from plant callus, explants, organs, pollens, embryos or parts thereof. Such regeneration techniques are described generally in Klee et al (1987) *Ann. Rev. of Plant Phys.* 38:467486.

The nucleic acids of the invention can be used to confer desired traits on essentially any plant. A wide variety of plants and plant cell systems may be engineered for the desired physiological and agronomic characteristics described herein using the nucleic acid constructs of the present invention and the various transformation methods mentioned above. In preferred embodiments, target plants and plant cells for engineering include, but are not limited to, those monocotyledonous and dicotyledonous plants, such as crops including grain crops (e.g., wheat, maize, rice, millet, barley), fruit crops (e.g., tomato, apple, pear, strawberry, orange), forage crops (e.g., alfalfa), root vegetable crops (e.g., carrot, potato, sugar beets, yam), leafy vegetable crops (e.g., lettuce, spinach); flowering plants (e.g., petunia, rose, chrysanthemum), conifers and pine trees (e.g., pine fir, spruce); plants used in phytoremediation (e.g., heavy metal accumulating plants); oil crops (e.g., corn, sunflower, rape seed) and plants used for experimental purposes (e.g., *Arabidopsis*). Thus, the invention has use over abroad range of plants, including, but not limited to, species from the genera *Asparagus, Avena, Brassica, Citrus, Citrullus, Capsicum, Cucurbita, Daucus, Glycine, Hordeum, Lactuca, Lycopersicon, Malus, Manihot, Nicotiana, Oryza, Persea, Pisum, Pyrus, Prunus, Raphanus, Secale, Solanum, Sorghum, Triticum, Vitis, Vigna*, and *Zea*.

One of skill in the art will recognize that after the expression cassette is stably incorporated in transgenic plants and confirmed to be operable, it can be introduced into other plants by sexual crossing. Any of a number of standard breeding techniques can be used, depending upon the species to be crossed.

A transformed plant cell, callus, tissue or plant may be identified and isolated by selecting or screening the engineered plant material for traits encoded by the marker genes present on the transforming DNA. For instance, selection may be performed by growing the engineered plant material on media containing an inhibitory amount of the antibiotic or herbicide to which the transforming gene construct confers resistance. Further, transformed plants and plant cells may also be identified by screening for the activities of any visible marker genes (e.g., the β-glucuronidase, luciferase, B or C1 genes) that may be present on the recombinant nucleic acid constructs of the present invention. Such selection and screening methodologies are well known to those skilled in the art.

Physical and biochemical methods also may be used to identify plant or plant cell transformants containing the gene constructs of the present invention. These methods include but are not limited to: 1) Southern analysis or PCR amplification for detecting and determining the structure of the recombinant DNA insert; 2) Northern blot, S1 RNase protection, primer-extension or reverse transcriptase-PCR amplification for detecting and examining RNA transcripts of the gene constructs; 3) enzymatic assays for detecting enzyme or ribozyme activity, where such gene products are encoded by the gene construct; 4) protein gel electrophoresis, Western blot techniques, immunoprecipitation, or enzyme-linked immunoassays, where the gene construct products are proteins. Additional techniques, such as in situ hybridization, enzyme staining, and immunostaining, also may be used to detect the presence or expression of the recombinant construct in specific plant organs and tissues. The methods for doing all these assays are well known to those skilled in the art.

Effects of gene manipulation using the methods of this invention can be observed by, for example, northern blots of the RNA (e.g., mRNA) isolated from the tissues of interest. Typically, if the amount of mRNA has increased, it can be assumed that the endogenous DWF12 gene is being expressed at a greater rate than before. Other methods of measuring DWF12 activity can be used. For example, cell length can be measured at specific times. Because DWF12 affects a BR signaling pathway, and dwf12 mutants ultimately accumulate a significant amount of BRs, such as brassinolide, an assay that measures the amount of a BR of interest can also be used. Such assays are known in the art. Different types of enzymatic assays can be used, depending on the substrate used and the method of detecting the increase or decrease of a reaction product or by-product. In addition, the levels of DWF12 protein expressed can be measured immunochemically, i.e., ELISA, RIA, EIA and other antibody based assays well known to those of skill in the art, by electrophoretic detection assays (either with staining or western blotting).

The transgene may be selectively expressed in some tissues of the plant or at some developmental stages, or the transgene may be expressed in substantially all plant tissues, substantially along its entire life cycle. However, any combinatorial expression mode is also applicable.

The present invention also encompasses seeds of the transgenic plants described above wherein the seed has the transgene or gene construct. The present invention further encompasses the progeny, clones, cell lines or cells of the transgenic plants described above wherein said progeny, clone, cell line or cell has the transgene or gene construct.

Polypeptides

The present invention also includes DWF12 polypeptides and mutants, including such polypeptides as a fusion, or chimeric protein product (comprising the protein, fragment, analog, mutant or derivative joined via a peptide bond to a heterologous protein sequence (of a different protein)). Such a chimeric product can be made by ligating the appropriate nucleic acid sequences encoding the desired amino acid sequences to each other by methods known in the art, in the proper coding frame, and expressing the chimeric product by methods commonly known in the art.

As noted above, a dwf12 phenotype as defined herein includes any macroscopic, microscopic or biochemical change which is characteristic of over- or under-expression of DWF12. Thus, a dwf12 mutant phenotype (e.g., activities) can include any in vitro, in vivo, biological, enzymatic, immunological, substrate binding activities, etc., as described above.

A dwf12 analog, whether a derivative, fragment or fusion of a native DWF12 polypeptide, is capable of at least one DWF12 activity. Preferably, the analogs exhibit increased or decreased SHAGGY kinase activity, such as no SHAGGY kinase activity to 10-fold or more activity.

Further, such analogs exhibit some sequence identity to the native DWF12 polypeptide sequence. Preferably, the variants will exhibit at least 35%, more preferably at least 50-60%, even more preferably 75% or 80% sequence identity, even more preferably 85% sequence identity, even more preferably, at least 90% sequence identity; more preferably at least 95%, 96%, 97%, 98% or 99% sequence identity.

dwf12 analogs can include derivatives with increased or decreased activities as compared to the native DWF12 polypeptides, as explained above. Such derivatives can include changes within the domains, motifs and/or consensus regions of the native DWF12 polypeptide, which are described in detail above.

Once class of analogs is those polypeptide sequences that differ from the native DWF12 polypeptide by changes, insertions, deletions, or substitution; at positions flanking the domain and/or conserved residues. For example, an analog can comprise (1) the domains of a DWF12 polypeptide and/or (2) residues conserved between the DWF12 polypeptide.

Another class of analogs includes those that comprise a DWF12 polypeptide sequence that differs from the native sequence in the domain of interest or conserved residues by a conservative substitution.

Yet another class of analogs includes those that lack one of the in vitro activities or structural features of the native DWF12 polypeptides, for example, dominant negative mutants or analogs that comprise a characteristic DWF12 domain but contain other inactivated domains.

DWF12 polypeptide fragments can comprise sequences from the native or analog sequences, for example fragments comprising one or more of the domains or regions shown in FIG. 3 and described in detail herein.

Fusion polypeptides comprising DWF12 polypeptides (e.g., native, analogs, or fragments thereof) can also be constructed. Non-limiting examples of other polypeptides that can be used in fusion proteins include chimeras of DWF12 polypeptides and fragments thereof; and related polypeptides or fragments thereof, such as those derived from the sequence shown in FIG. 3, for example, a fusion between amino acids 1-37 of the DWF12 sequence with other unrelated sequences, to modulate a BR signaling pathway.

DWF12 polypeptides, derivatives (including fragments and chimeric proteins), mutants and analogues may be recombinantly produced, as described above, or can be chemically synthesized. See, e.g., Clark-Lewis et al. (1991) *Biochem.* 30:3128-3135 and Merrifield (1963) *J. Amer. Chem. Soc.* 85:2149-2156. For example, DWF12, derivatives, mutants and analogs can be synthesized by solid phase techniques, cleaved from the resin, and purified by preparative high performance liquid chromatography (e.g., see Creighton, 1983, Proteins, Structures and Molecular Principles, W. H. Freeman and Co., N.Y., pp. 50-60). DWF12, derivatives and analogs that are proteins can also be synthesized by use of a peptide synthesizer. The composition of the synthetic peptides may be confirmed by amino acid analysis or sequencing (e.g., the Edman degradation procedure; see Creighton, 1983, Proteins, Structures and Molecular Principles, W. H. Freeman and Co., N.Y., pp. 34-49).

Further, the polynucleotides, polypeptides and mutants thereof described herein can be used to generate antibodies that specifically recognize and bind to the protein products of the described polynucleotides. (See, Harlow and Lane, eds. (1988) "Antibodies: A Laboratory Manual"). The polypeptides and mutant polypeptides and antibodies thereto can also be used in standard diagnostic assays, for example, radioimmunoassays, ELISA (enzyme linked immunoradiometric assays), "sandwich" immunoassays, immunoradiometric assays, in situ immunoassay, western blot analysis, immunoprecipitationassays, immunofluorescent assays and SDS-PAGE.

Applications

The present invention finds use in various applications, for example, including but not limited to those listed above.

The polynucleotide sequences may additionally be used to isolate mutant dwf12 gene alleles. Such mutant alleles may be isolated from plant species either known or proposed to have a genotype which contributes to altered plant morphology. Additionally, such plant dwf12 gene sequences can be used to detect plant dwf12 gene regulatory (e.g., promoter or promotor/enhancer) defects which can affect plant growth.

The molecules of the present invention can be used to provide plants with increased seed and/or fruit production, extended flowering periods and increased branching. The molecules described herein can be used to alter the sterol composition of a plant, thereby increasing or reducing cholesterol content in the plant. A still further utility of the molecules of the present invention is to provide a tool for studying the biosynthesis of brassinosteriods, both in vitro and in vivo.

The polynucleotides of the invention also have utility as a transgene encoding a protein that mediates one or more steps in the brassinosteriod signaling pathway which results in a transgenic plant with altered biochemical properties, plant structure or morphology. The mutant genes also have utility for encoding the mutant proteins in recombinant vectors which may be inserted into host cells to express the protein. Further, the polynucleotides of the invention may be utilized (1) as nucleic acid probes to screen nucleic acid libraries to identify other enzymatic genes or mutants; (2) as nucleic acid sequences to be mutated or modified to produce protein variants or derivatives; (3) as nucleic acids encoding DWF12 and other SHAGGY kinases in molecular biology techniques or industrial applications commonly known to those skilled in the art.

The DWF12 molecules and mutant dwf12 nucleic acid molecules may be used to design antisense molecules, useful, for example, in gene regulation or as antisense primers in amplification reactions of DWF12 and other SHAGGY kinase nucleic acid sequences. Such techniques can be used to regulate, for example, plant growth, development or gene expression. Further, such sequences may be used as part of ribozyme and/or triple helix sequences, also useful for gene regulation.

The DWF12 control element (e.g., promoter) may be utilized as a plant promoter to express any protein, polypeptide or peptide of interest in a transgenic plant. In particular, the DWF12 promoter may be used to express a protein involved in brassinosteriod biosynthesis.

The DWF12 proteins and mutants of the invention can be used in any biochemical applications (experimental or industrial) where modulation of BRs, such as but not limited to brassinolide production, modification of elongating plant structures, and experimental or industrial biochemical applications known to those skilled in the art.

III. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

EXAMPLE 1

Phenotypes of dwf12 Mutants dwf12-1 and dwf12-2 plants were generated by EMS (ethylmethanesulfonate) mutagenisis using techniques well known in the art. The mutants were identified due to their characteristic dwarf phenotype. dwf12-1 and dwf12-2 plants were compared to a BR-biosynthetic mutant, dwf4-1, and BR-insensitive mutants bri1 and twisted (twd). The phenotypes of the two dwf12 alleles were similar to dwf4 and bri1 plants in that they all displayed dark green and round leaves, short and sturdier stature relative to wild type (Ws-2). A unique phenotype found only in dwf12 mutants was severe downward curling of leaves. Plants heterozygous for dwf12 mutations showed a semi-dwarf phenotype with a height intermediate between wild-type and homozygous mutant plants, suggesting that the dwf12 mutations are dominant-negative, gain of function, or haploinsufficient. Further morphometric analysis of the two dwf12 alleles, dwf12-1 and dwf12-2, indicated that the dwf12-2 mutations resulted in more severe phenotypes than those of dwf12-1. Silique comparison showed that dwf12 mutations caused reduced fertility (short silique) and fecundity, suggesting that DWF12 activity is required for seed development.

EXAMPLE 2

Ectopic Overexpression of DWF12

Previously, we found that ectopic overexpression of the DWF4 gene encoding a rate-limiting step enzyme in the BR biosynthetic pathways resulted in bigger plants due to elongated cell size. Thus, the same approach was used to examine the effects contributed by DWF12 overexpression. A vector comprising the 35S promoter operably linked to wild-type DWF12 cDNA was compared to a vector control harboring only a vector. 11 independent transformants (AOD12) carrying the DWF12 overexpression construct consistently displayed a bigger plant phenotype, such as long petiole, elongated leaf blades, bigger flowers and weaker inflorescences. The bigger plant phenotypes of AOD12 suggests that the DWF12 gene is transcriptionally controlled, and this regulation is important in determining the cell sizes and whole plant morphology in *Arabidopsis*.

Thus, DWF12 sequences, polypeptides, mutants thereof and uses of these molecules are described. From the foregoing, it will be appreciated that, although specific embodiments of the invention have been described herein for purposes of illustration, various modifications may be made without deviating from the spirit and scope of the invention as defined by the appended claims.

SEQUENCE LISTING

```
<160> NUMBER OF SEQ ID NOS: 13

<210> SEQ ID NO 1
<211> LENGTH: 2787
<212> TYPE: DNA
<213> ORGANISM: Artificial Sequence
<220> FEATURE:
<223> OTHER INFORMATION: Genomic sequence of DWF12 locus

<400> SEQUENCE: 1
agaaagagaa agagaagagc tggattcaca tggtcttgtt ctttctctct ccttcttttc      60
tcatcttgcg gcttcccttt ctctctctat cgccacaatg atcattacca accaaactga     120
ttgaaactca tttgttctct ctctctcaaa tccactctct ctctttcttt tctcttctcc     180
tctctgtgtc tctatcgcca tggctgatga taaggtaaag ctgcttgtgt tccttttgct     240
gtcttttgaa gaagaagatc ctgttttttg gtttttccac atttgaccct tcaattagtt     300
```

```
gtcttgagat tcctgttctt acagatgttt tgtgataata atctagtttt agttagtact       360
cttgaagttg aacggttttg agttctgggt ttgtccaaag ttttgagctt tcgttaactt       420
tttgacttac cctgagatct ctgagggttt tgagttctga gcttagaatt ttctaagtta       480
gctctgttgg gatgatccat gtctatatat ctcgatctgt gattaatcca gagtttatac       540
aagctgctag atccataatt gaacatagat tagtccttgt ttggtttgtt atatgtattt       600
gttttgttta ccattctttt ggcgtgacaa agtatatat ttttagtttt aactaaatca        660
gattcactct gcgtaacggt tattttgtaa ccactctttt aggataaaag tttccttctt       720
tagacttttg attctcagac aagcattatt cttttagctt ttgataatgg ttttgtgctg       780
atattaaagc ttttctcttt caggagatgc ctgctgctgt agttgatgga catgatcaag       840
tcactggtca tattatttcc accacaatcg gtggcaaaaa tggtgaacca aaacaggtat       900
ttttaaggct tttaaccaaa tagactcact tttatgtata tgcaagatt tgatggttac       960 caatacattt ttctatgttg ttgttagaca attagttaca tggcggagcg agttgttggt       1020
acaggctcgt tcgggatcgt tttccaagca aaatgtttgg agactggaga aaccgtggcg       1080
ataaagaagg ttttgcaaga tagaagatac aagaaccgag aacttcagtt gatgcgtgtg       1140
atggatcatc cgaatgtggt ttgtttgaag cattgcttct tttcgactac aagtaaagac       1200
gagcttttct tgaacttggt tatggagtat gtccctgaga gcttgtatcg agttctgaaa       1260
cattatagta gtgcaaacca aagaatgcct cttgtctatg ttaaacttta catgtatcag       1320
gtaataacaa cacacattca tatcttccat ttccaaagtt gatgtacata agattgttct       1380
tatgctgata ttacttcctt ttgttatgtt agatcttccg gggacttgct tacattcaca       1440
atgttgctgg agtttgtcac agagatctaa agcctcaaaa tcttctggta tgtgtaacat       1500
tttaagattg aactctttgt ttttttctt gcctttgttt ctttcgttct taatgtatct       1560
cttctggtct ctttctatag gttgatcctc ttactcatca agtcaaaatc tgtgactttg       1620
gcagtgcgaa acagctcgta agactttgtg acatataaac tcattcgact tgtagcggtt       1680
gttgttttct gtgatcttgt catttactgt tgaaatctac ttttgcttca ggttaaaggt       1740
gaagccaaca tttcttacat ctgctcacga ttctaccgtg cacccgagct catatttggt       1800
gccactgagt acacaacttc tattgatatc tggtctgctg gttgtgttct tgctgagctt       1860
cttcttggtc aggtaaacaa ttctttcagt aaccagctta ttcaatctcc atgtgtatat       1920
ttgcattagg actcattgtg actatatcat gttcttatgc agccattatt tcccggagaa       1980
aatgctgtgg atcagctcgt tgaaattata aagtaagaa tctttaaacg atgattcctt        2040
gcaaattaca ttctttggct acaaaatcct cactgtatag ttgttgtaca caggttcttg       2100
gtacaccaac tcgagaagaa atccgttgta tgaatccaca ttacacagat ttcaggtttc       2160
cacagataaa ggcacatccc tggcacaagg ttagtgtctt ttctcttttt gcatgtgttc       2220
ttgtttcagt ttctttcttc acacatcaac tgatcataat tacgttttgg tttagatctt       2280
ccacaaaagg atgcccccag aagcgattga ttttgcatca aggctgcttc aatactctcc       2340
aagtctaaga tgcacagcgg taagcattgg tcttgaggtt tcttcagtct ctaagaatcc       2400
aactgaatcc ttactatata ttttgtttcc tcgtatttca gctcgaagct tgtgcacatc       2460
cgttctttga tgaactcaga gaaccaaacg ctcgtttacc aaatggacgg cctttcccgc       2520
ctctcttcaa cttcaaacaa gaagtagctg atcatcacc tgaactggtc aacaagttga       2580
ttccagacca tatcaagaga caattgggtc taagcttctt gaatcaatct ggaacttaaa      2640
```

-continued

```
agggatcctg caaaagacaa ctactttttt atatataatg taccattaca cgagccacaa    2700
ggtcgtagtt gaaggcaaac gtggaggaca caattcaaag tttttcctcc tcaaactcgt    2760
tcagacaaag ccagctgcta gcaaaac                                        2787
```

<210> SEQ ID NO 2
<211> LENGTH: 5
<212> TYPE: PRT
<213> ORGANISM: Artificial Sequence
<220> FEATURE:
<223> OTHER INFORMATION: Exon number 1

<400> SEQUENCE: 2

Met Ala Asp Asp Lys
1               5

<210> SEQ ID NO 3
<211> LENGTH: 31
<212> TYPE: PRT
<213> ORGANISM: Artificial Sequence
<220> FEATURE:
<223> OTHER INFORMATION: Exon number 2

<400> SEQUENCE: 3

Glu Met Pro Ala Ala Val Val Asp Gly His Asp Gln Val Thr Gly His
1               5                   10                  15

Ile Ile Ser Thr Thr Ile Gly Gly Lys Asn Gly Glu Pro Lys Gln
            20                  25                  30

<210> SEQ ID NO 4
<211> LENGTH: 111
<212> TYPE: PRT
<213> ORGANISM: Artificial Sequence
<220> FEATURE:
<223> OTHER INFORMATION: Exon number 3

<400> SEQUENCE: 4

Thr Ile Ser Tyr Met Ala Glu Arg Val Val Gly Thr Gly Ser Phe Gly
1               5                   10                  15

Ile Val Phe Gln Ala Lys Cys Leu Glu Thr Gly Glu Thr Val Ala Ile
            20                  25                  30

Lys Lys Val Leu Gln Asp Arg Arg Tyr Lys Asn Arg Glu Leu Gln Leu
        35                  40                  45

Met Arg Val Met Asp His Pro Asn Val Cys Leu Lys His Cys Phe
    50                  55                  60

Phe Ser Thr Thr Ser Lys Asp Glu Leu Phe Leu Asn Leu Val Met Glu
65                  70                  75                  80

Tyr Val Pro Glu Ser Leu Tyr Arg Val Leu Lys His Tyr Ser Ser Ala
                85                  90                  95

Asn Gln Arg Met Pro Leu Val Tyr Val Lys Leu Tyr Met Tyr Gln
            100                 105                 110

<210> SEQ ID NO 5
<211> LENGTH: 25
<212> TYPE: PRT
<213> ORGANISM: Artificial Sequence
<220> FEATURE:
<223> OTHER INFORMATION: Exon number 4

<400> SEQUENCE: 5

Ile Phe Arg Gly Leu Ala Tyr Ile His Asn Val Ala Gly Val Cys His
1               5                   10                  15

-continued

Arg Asp Leu Lys Pro Gln Asn Leu Leu
         20              25

<210> SEQ ID NO 6
<211> LENGTH: 19
<212> TYPE: PRT
<213> ORGANISM: Artificial Sequence
<220> FEATURE:
<223> OTHER INFORMATION: Exon number 5

<400> SEQUENCE: 6

Val Asp Pro Leu Thr His Gln Val Lys Ile Cys Asp Phe Gly Ser Ala
 1               5                  10                  15

Lys Gln Leu

<210> SEQ ID NO 7
<211> LENGTH: 47
<212> TYPE: PRT
<213> ORGANISM: Artificial Sequence
<220> FEATURE:
<223> OTHER INFORMATION: Exon number 6

<400> SEQUENCE: 7

Val Lys Gly Glu Ala Asn Ile Ser Tyr Ile Cys Ser Arg Phe Tyr Arg
 1               5                  10                  15

Ala Pro Glu Leu Ile Phe Gly Ala Thr Glu Tyr Thr Thr Ser Ile Asp
            20                  25                  30

Ile Trp Ser Ala Gly Cys Val Leu Ala Glu Leu Leu Leu Gly Gln
        35                  40                  45

<210> SEQ ID NO 8
<211> LENGTH: 17
<212> TYPE: PRT
<213> ORGANISM: Artificial Sequence
<220> FEATURE:
<223> OTHER INFORMATION: Exon number 7

<400> SEQUENCE: 8

Pro Leu Phe Pro Gly Glu Asn Ala Val Asp Gln Leu Val Glu Ile Ile
 1               5                  10                  15

Lys

<210> SEQ ID NO 9
<211> LENGTH: 32
<212> TYPE: PRT
<213> ORGANISM: Artificial Sequence
<220> FEATURE:
<223> OTHER INFORMATION: Exon number 8

<400> SEQUENCE: 9

Val Leu Gly Thr Pro Thr Arg Glu Glu Ile Arg Cys Met Asn Pro His
 1               5                  10                  15

Tyr Thr Asp Phe Arg Phe Pro Gln Ile Lys Ala His Pro Trp His Lys
            20                  25                  30

<210> SEQ ID NO 10
<211> LENGTH: 28
<212> TYPE: PRT
<213> ORGANISM: Artificial Sequence
<220> FEATURE:
<223> OTHER INFORMATION: Exon number 9

<400> SEQUENCE: 10

Ile Phe His Lys Arg Met Pro Pro Glu Ala Ile Asp Phe Ala Ser Arg

```
                1               5                   10                  15
Leu Leu Gln Tyr Ser Pro Ser Leu Arg Cys Thr Ala
                20                  25

<210> SEQ ID NO 11
<211> LENGTH: 65
<212> TYPE: PRT
<213> ORGANISM: Artificial Sequence
<220> FEATURE:
<223> OTHER INFORMATION: Exon number 10

<400> SEQUENCE: 11

Leu Glu Ala Cys Ala His Pro Phe Phe Asp Glu Leu Arg Glu Pro Asn
 1               5                   10                  15

Ala Arg Leu Pro Asn Gly Arg Pro Phe Pro Pro Leu Phe Asn Phe Lys
            20                  25                  30

Gln Glu Val Ala Gly Ser Ser Pro Glu Leu Val Asn Lys Leu Ile Pro
        35                  40                  45

Asp His Ile Lys Arg Gln Leu Gly Leu Ser Phe Leu Asn Gln Ser Gly
    50                  55                  60

Thr
65

<210> SEQ ID NO 12
<211> LENGTH: 1490
<212> TYPE: DNA
<213> ORGANISM: Artificial Sequence
<220> FEATURE:
<223> OTHER INFORMATION: A DWF12 cDNA

<400> SEQUENCE: 12
```

| | | | | | |
|---|---|---|---|---|---|
| agaaagagaa | agagaagagc | tggattcaca | tggtcttgtt | ctttctctct | ccttcttttc | 60 |
| tcatcttgcg | gcttcccttt | ctctctctat | cgccacaatg | atcattacca | accaaactga | 120 |
| ttgaaactca | tttgttctct | ctctctcaaa | tccactctct | ctctttcttt | tctcttctcc | 180 |
| tctctgtgtc | tctatcgcca | tggctgatga | taaggagatg | cctgctgctg | tagttgatgg | 240 |
| acatgatcaa | gtcactggtc | atattatttc | caccacaatc | ggtggcaaaa | atggtgaacc | 300 |
| aaaacagaca | attagttaca | tggcggagcg | agttgttggt | acaggctcgt | tcgggatcgt | 360 |
| tttccaagca | aaatgtttgg | agactggaga | accgtggcg | ataagaagg | ttttgcaaga | 420 |
| tagaagatac | aagaaccgag | aacttcagtt | gatgcgtgtg | atggatcatc | cgaatgtggt | 480 |
| ttgtttgaag | cattgcttct | tttcgactac | aagtaaagac | gagcttttct | tgaacttggt | 540 |
| tatggagtat | gtccctgaga | gcttgtatcg | agttctgaaa | cattatagta | gtgcaaacca | 600 |
| aagaatgcct | cttgtctatg | ttaaacttta | catgtatcga | atcttccggg | gacttgctta | 660 |
| cattcacaat | gttgctggag | tttgtcacag | agatctaaag | cctcaaaatc | ttctggttga | 720 |
| tcctcttact | catcaagtca | aaatctgtga | ctttggcagt | gcgaaacagc | tcgttaaagg | 780 |
| tgaagccaac | atttcttaca | tctgctcacg | attctaccgt | gcacccgagc | tcatatttgg | 840 |
| tgccactgag | tacacaactt | ctattgatat | ctggtctgct | ggttgtgttc | ttgctgagct | 900 |
| tcttcttggt | cagccattat | ttccggaga | aaatgctgtg | gatcagctcg | ttgaaattat | 960 |
| aaaagttctt | ggtacaccaa | ctcgagaaga | aatccgttgt | atgaatccac | attcacaga | 1020 |
| tttcaggttt | ccacagataa | aggcacatcc | ctggcacaag | atcttccaca | aaaggatgcc | 1080 |
| cccagaagcg | attgattttg | catcaaggct | gcttcaatac | tctccaagtc | taagatgcac | 1140 |
| agcgctcgaa | gcttgtgcac | atccgttctt | tgatgaactc | agagaaccaa | acgctcgttt | 1200 |

```
accaaatgga cggcctttcc cgcctctctt caacttcaaa caagaagtag ctggatcatc    1260
acctgaactg gtcaacaagt tgattccaga ccatatcaag agacaattgg gtctaagctt    1320
cttgaatcaa tctggaactt aaaagggatc ctgcaaaaga caactacttt tttatatata    1380
atgtaccatt acacgagcca caggtcgta gttgaaggca acgtggagg acacaattca       1440 aagttttttcc tcctcaaact cgttcagaca agccagctg ctagcaaaac                1490
```

<210> SEQ ID NO 13
<211> LENGTH: 380
<212> TYPE: PRT
<213> ORGANISM: Artificial Sequence
<220> FEATURE:
<223> OTHER INFORMATION: DWF12

<400> SEQUENCE: 13

Met Ala Asp Asp Lys Glu Met Pro Ala Ala Val Val Asp Gly His Asp
1               5                   10                  15

Gln Val Thr Gly His Ile Ile Ser Thr Thr Ile Gly Gly Lys Asn Gly
            20                  25                  30

Glu Pro Lys Gln Thr Ile Ser Tyr Met Ala Glu Arg Val Val Gly Thr
        35                  40                  45

Gly Ser Phe Gly Ile Val Phe Gln Ala Lys Cys Leu Glu Thr Gly Glu
    50                  55                  60

Thr Val Ala Ile Lys Lys Val Leu Gln Asp Arg Arg Tyr Lys Asn Arg
65                  70                  75                  80

Glu Leu Gln Leu Met Arg Val Met Asp His Pro Asn Val Val Cys Leu
                85                  90                  95

Lys His Cys Phe Phe Ser Thr Thr Ser Lys Asp Glu Leu Phe Leu Asn
            100                 105                 110

Leu Val Met Glu Tyr Val Pro Glu Ser Leu Tyr Arg Val Leu Lys His
        115                 120                 125

Tyr Ser Ser Ala Asn Gln Arg Met Pro Leu Val Tyr Val Lys Leu Tyr
    130                 135                 140

Met Tyr Gln Ile Phe Arg Gly Leu Ala Tyr Ile His Asn Val Ala Gly
145                 150                 155                 160

Val Cys His Arg Asp Leu Lys Pro Gln Asn Leu Leu Val Asp Pro Leu
                165                 170                 175

Thr His Gln Val Lys Ile Cys Asp Phe Gly Ser Ala Lys Gln Leu Val
            180                 185                 190

Lys Gly Glu Ala Asn Ile Ser Tyr Ile Cys Ser Arg Phe Tyr Arg Ala
        195                 200                 205

Pro Glu Leu Ile Phe Gly Ala Thr Glu Tyr Thr Thr Ser Ile Asp Ile
    210                 215                 220

Trp Ser Ala Gly Cys Val Leu Ala Glu Leu Leu Leu Gly Gln Pro Leu
225                 230                 235                 240

Phe Pro Gly Glu Asn Ala Val Asp Gln Leu Val Glu Ile Ile Lys Val
                245                 250                 255

Leu Gly Thr Pro Thr Arg Glu Glu Ile Arg Cys Met Asn Pro His Tyr
            260                 265                 270

Thr Asp Phe Arg Phe Pro Gln Ile Lys Ala His Pro Trp His Lys Ile
        275                 280                 285

Phe His Lys Arg Met Pro Pro Glu Ala Ile Asp Phe Ala Ser Arg Leu
    290                 295                 300

Leu Gln Tyr Ser Pro Ser Leu Arg Cys Thr Ala Leu Glu Ala Cys Ala

-continued

```
             305                 310                 315                 320

His Pro Phe Phe Asp Glu Leu Arg Glu Pro Asn Ala Arg Leu Pro Asn
                 325                 330                 335

Gly Arg Pro Phe Pro Pro Leu Phe Asn Phe Lys Gln Glu Val Ala Gly
                 340                 345                 350

Ser Ser Pro Glu Leu Val Asn Lys Leu Ile Pro Asp His Ile Lys Arg
                 355                 360                 365

Gln Leu Gly Leu Ser Phe Leu Asn Gln Ser Gly Thr
                 370                 375                 380
```

The invention claimed is:

1. A transgenic plant having a recombinant nucleic acid construct comprising a polynucleotide comprising a nucleic acid sequence encoding a polypeptide having at least 95% sequence identity to the amino acid sequence set forth in SEQ ID NO:13 and one or more tissue-specific or inducible control elements operably linked to said nucleic acid sequence, wherein said transgenic plant has an altered phenotype relative to a corresponding wild-type plant, wherein said altered phenotype is selected from the group consisting of increased plant size and elongated leaf blades.

2. A method of making a transgenic plant comprising introducing a polynucleotide comprising a nucleic acid sequence encoding a polypeptide having at least 95% sequence identity to the amino acid sequence set forth in SEQ ID NO:13 and one or more tissue-specific or inducible control elements operably linked to said nucleic acid sequence into a plant cell to produce a transformed plant cell and producing a transgenic plant from said transformed plant cell, wherein said transgenic plant has an altered phenotype relative to a corresponding wild-type plant, wherein said altered phenotype is selected from the group consisting of increased plant size and elongated leaf blades.

3. The method of claim 2, wherein altered phenotype is elongated leaf blades.

4. A method of modulating a phenotype in a transgenic plant, said method comprising expressing a polynucleotide comprising a nucleic acid sequence encoding a polypeptide having at least 95% sequence identity to the amino acid sequence set forth in SEQ ID NO:13 and one or more tissue-specific or inducible control elements operably linked to said nucleic acid sequence in a plant, said transgenic plant having an altered phenotype relative to a corresponding wild-type plant, wherein said altered phenotype is selected from the group consisting of increased plant size and elongated leaf blades.

5. The method of claim 2, wherein said one or more control elements comprise a tissue-specific promoter.

6. The method of claim 5, wherein said tissue-specific promoter is operably linked in sense orientation to said coding sequence.

7. The transgenic plant of claim 1, wherein said sequence identity is at least 97%.

8. The transgenic plant of claim 1, wherein said sequence identity is 100%.

9. The method of claim 2, wherein said sequence identity is at least 97%.

10. The method of claim 2, wherein said sequence identity is 100%.

11. The method of claim 4, wherein said sequence identity is at least 97%.

12. The method of claim 4, wherein said sequence identity is 100%.

* * * * *

UNITED STATES PATENT AND TRADEMARK OFFICE
CERTIFICATE OF CORRECTION

PATENT NO.        : 7,304,205 B2                                    Page 1 of 1
APPLICATION NO.   : 10/477687
DATED             : December 4, 2007
INVENTOR(S)       : Sunghwa Choe It is certified that error appears in the above-identified patent and that said Letters Patent is hereby corrected as shown below:

Column 1, line 12 insert the following new paragraph:

--STATEMENT AS TO FEDERALLY SPONSORED RESEARCH

This invention was made with government support under grant number 97-35304-4708 awarded by USDA/NIFA. The government has certain rights in the invention.--, therefor.

Column 42, line 30 (Claim 6), please delete "coding" and insert --nucleic acid--, therefor.

Signed and Sealed this
Twelfth Day of June, 2012

David J. Kappos
*Director of the United States Patent and Trademark Office*